(12) United States Patent
Shelton, IV et al.

(10) Patent No.: US 8,858,571 B2
(45) Date of Patent: Oct. 14, 2014

(54) HYDRAULICALLY AND ELECTRICALLY ACTUATED ARTICULATION JOINTS FOR SURGICAL INSTRUMENTS

(75) Inventors: Frederick E. Shelton, IV, Hillsboro, OH (US); Jeffrey S. Swayze, Hamilton, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1159 days.

(21) Appl. No.: 12/731,347

(22) Filed: Mar. 25, 2010

(65) Prior Publication Data

US 2010/0179382 A1 Jul. 15, 2010

Related U.S. Application Data

(62) Division of application No. 11/270,866, filed on Nov. 9, 2005, now abandoned.

(51) Int. Cl.
| | |
|---|---|
| A61B 17/10 | (2006.01) |
| A61B 17/072 | (2006.01) |
| A61B 17/00 | (2006.01) |
| A61B 17/29 | (2006.01) |

(52) U.S. Cl.
CPC ..... *A61B 17/07207* (2013.01); *A61B 2017/003* (2013.01); *A61B 2017/00017* (2013.01); *A61B 2017/00535* (2013.01); *A61B 2017/00398* (2013.01); *A61B 2017/2901* (2013.01); *A61B 2017/2927* (2013.01); *A61B 2017/00367* (2013.01); *A61B 17/29* (2013.01); *A61B 2017/2925* (2013.01)
USPC .......... 606/142; 227/175.1; 600/142

(58) Field of Classification Search
USPC .................. 606/139–151, 167, 170; 600/101, 600/139–150
See application file for complete search history.

(56) References Cited

U.S. PATENT DOCUMENTS

| | | | |
|---|---|---|---|
| 1,794,907 | A | 3/1931 | Kelly |
| 3,551,987 | A | 1/1971 | Wilkinson |
| 4,180,285 | A | 12/1979 | Reneau |
| 4,499,895 | A * | 2/1985 | Takayama ..................... 600/148 |
| 4,505,273 | A | 3/1985 | Braun et al. |
| 4,655,222 | A | 4/1987 | Florez et al. |
| 4,809,695 | A | 3/1989 | Gwathmey et al. |
| 4,844,068 | A | 7/1989 | Arata et al. |
| 5,005,754 | A | 4/1991 | Van Overloop |

(Continued)

FOREIGN PATENT DOCUMENTS

| | | |
|---|---|---|
| CA | 2458946 A1 | 3/2003 |
| CA | 2512960 A1 | 1/2006 |

(Continued)

OTHER PUBLICATIONS

European Search Report, Application No. 06255736.8, dated Oct. 2, 2007 (5 pages).

(Continued)

*Primary Examiner* — Corrine M McDermott
*Assistant Examiner* — Jing Ou

(57) ABSTRACT

Articulation joints for use in connection with a surgical instrument that has a portion that must be passed through a trocar or similar structure and then articulated relative to another portion of the instrument received within the trocar. Various embodiments of the articulation joint include at least one flexible driven member to articulate the surgical implement relative to the handle assembly of the instrument.

8 Claims, 17 Drawing Sheets

(56) References Cited

U.S. PATENT DOCUMENTS

| | | | |
|---|---|---|---|
| 5,009,661 A | 4/1991 | Michelson | |
| 5,018,657 A | 5/1991 | Pedlick et al. | |
| 5,042,707 A | 8/1991 | Taheri | |
| 5,071,430 A | 12/1991 | de Salis et al. | |
| 5,084,057 A | 1/1992 | Green et al. | |
| 5,108,368 A * | 4/1992 | Hammerslag et al. | 604/528 |
| 5,116,349 A | 5/1992 | Aranyi | |
| 5,139,513 A | 8/1992 | Segato | |
| 5,158,567 A | 10/1992 | Green | |
| 5,171,247 A | 12/1992 | Hughett et al. | |
| 5,171,249 A | 12/1992 | Stefanchik et al. | |
| 5,207,697 A | 5/1993 | Carusillo et al. | |
| 5,209,747 A * | 5/1993 | Knoepfler | 606/16 |
| 5,211,649 A | 5/1993 | Kohler et al. | |
| 5,219,111 A | 6/1993 | Bilotti et al. | |
| 5,222,975 A | 6/1993 | Crainich | |
| 5,236,440 A | 8/1993 | Hlavacek | |
| 5,258,009 A | 11/1993 | Conners | |
| 5,275,608 A | 1/1994 | Forman et al. | |
| 5,282,806 A | 2/1994 | Haber et al. | |
| 5,282,829 A | 2/1994 | Hermes | |
| 5,304,204 A | 4/1994 | Bregen | |
| 5,314,466 A | 5/1994 | Stern et al. | |
| 5,342,395 A | 8/1994 | Jarrett et al. | |
| 5,342,396 A | 8/1994 | Cook | |
| 5,350,391 A | 9/1994 | Iacovelli | |
| 5,350,400 A | 9/1994 | Esposito et al. | |
| 5,366,479 A | 11/1994 | McGarry et al. | |
| 5,368,592 A * | 11/1994 | Stern et al. | 606/33 |
| 5,383,880 A | 1/1995 | Hooven | |
| 5,397,324 A | 3/1995 | Carroll et al. | |
| 5,405,072 A | 4/1995 | Zlock et al. | |
| 5,405,344 A * | 4/1995 | Williamson et al. | 606/1 |
| 5,413,107 A * | 5/1995 | Oakley et al. | 600/463 |
| 5,413,272 A | 5/1995 | Green et al. | |
| 5,425,745 A | 6/1995 | Green et al. | |
| 5,449,365 A | 9/1995 | Green et al. | |
| 5,454,827 A | 10/1995 | Aust et al. | |
| 5,465,895 A | 11/1995 | Knodel et al. | |
| 5,474,566 A | 12/1995 | Alesi et al. | |
| 5,478,354 A | 12/1995 | Tovey et al. | |
| 5,480,089 A | 1/1996 | Blewett | |
| 5,482,197 A | 1/1996 | Green et al. | |
| 5,484,451 A | 1/1996 | Akopov et al. | |
| 5,485,952 A | 1/1996 | Fontayne | |
| 5,487,499 A | 1/1996 | Sorrentino et al. | |
| 5,497,933 A | 3/1996 | DeFonzo et al. | |
| 5,505,363 A | 4/1996 | Green et al. | |
| 5,529,235 A | 6/1996 | Boiarski et al. | |
| 5,535,934 A | 7/1996 | Boiarski et al. | |
| 5,540,375 A | 7/1996 | Bolanos et al. | |
| 5,542,594 A | 8/1996 | McKean et al. | |
| 5,554,169 A | 9/1996 | Green et al. | |
| 5,562,241 A | 10/1996 | Knodel et al. | |
| 5,562,682 A | 10/1996 | Oberlin et al. | |
| 5,564,615 A | 10/1996 | Bishop et al. | |
| 5,569,270 A * | 10/1996 | Weng | 606/144 |
| 5,571,116 A | 11/1996 | Bolanos et al. | |
| 5,575,799 A | 11/1996 | Bolanos et al. | |
| 5,575,805 A * | 11/1996 | Li | 606/206 |
| 5,577,654 A | 11/1996 | Bishop | |
| 5,582,617 A | 12/1996 | Klieman et al. | |
| 5,588,579 A | 12/1996 | Schnut et al. | |
| 5,601,224 A | 2/1997 | Bishop et al. | |
| 5,603,443 A | 2/1997 | Clark et al. | |
| 5,607,094 A | 3/1997 | Clark et al. | |
| 5,609,285 A | 3/1997 | Grant et al. | |
| 5,624,452 A | 4/1997 | Yates | |
| 5,626,595 A | 5/1997 | Sklar et al. | |
| 5,628,446 A | 5/1997 | Geiste et al. | |
| 5,630,539 A | 5/1997 | Plyley et al. | |
| 5,639,008 A | 6/1997 | Gallagher et al. | |
| 5,649,937 A | 7/1997 | Bito et al. | |
| 5,651,491 A | 7/1997 | Heaton et al. | |
| 5,653,373 A | 8/1997 | Green et al. | |
| 5,662,258 A | 9/1997 | Knodel et al. | |
| 5,667,527 A | 9/1997 | Cook | |
| 5,673,840 A | 10/1997 | Schulze et al. | |
| 5,673,841 A | 10/1997 | Schulze et al. | |
| 5,680,981 A | 10/1997 | Mililli et al. | |
| 5,680,982 A | 10/1997 | Schulze et al. | |
| 5,692,668 A | 12/1997 | Schulze et al. | |
| 5,700,270 A | 12/1997 | Peyser et al. | |
| 5,702,408 A | 12/1997 | Wales et al. | |
| 5,704,534 A | 1/1998 | Huitema et al. | |
| 5,711,472 A | 1/1998 | Bryan | |
| 5,715,987 A | 2/1998 | Kelley et al. | |
| 5,716,366 A | 2/1998 | Yates | |
| 5,725,536 A | 3/1998 | Oberlin et al. | |
| 5,725,554 A | 3/1998 | Simon et al. | |
| 5,730,758 A | 3/1998 | Allgeyer | |
| 5,732,871 A | 3/1998 | Clark et al. | |
| 5,752,644 A | 5/1998 | Bolanos et al. | |
| 5,758,814 A | 6/1998 | Gallagher et al. | |
| 5,792,165 A | 8/1998 | Klieman et al. | |
| 5,797,536 A | 8/1998 | Smith et al. | |
| 5,797,537 A | 8/1998 | Oberlin et al. | |
| 5,833,695 A | 11/1998 | Yoon | |
| 5,836,503 A | 11/1998 | Ehrenfels et al. | |
| 5,836,960 A | 11/1998 | Kolesa et al. | |
| 5,839,639 A | 11/1998 | Sauer et al. | |
| 5,843,169 A | 12/1998 | Taheri | |
| 5,865,361 A | 2/1999 | Milliman et al. | |
| 5,868,760 A | 2/1999 | McGuckin, Jr. | |
| 5,871,135 A | 2/1999 | Williamson IV et al. | |
| 5,897,562 A | 4/1999 | Bolanos et al. | |
| 5,899,914 A | 5/1999 | Zirps et al. | |
| 5,906,625 A | 5/1999 | Bito et al. | |
| 5,908,427 A | 6/1999 | McKean et al. | |
| 5,911,353 A | 6/1999 | Bolanos et al. | |
| 5,919,198 A | 7/1999 | Graves, Jr. et al. | |
| 5,931,847 A | 8/1999 | Bittner et al. | |
| 5,938,667 A | 8/1999 | Peyser et al. | |
| 5,941,442 A | 8/1999 | Geiste et al. | |
| 6,033,427 A | 3/2000 | Lee | |
| 6,045,560 A | 4/2000 | McKean et al. | |
| 6,077,286 A | 6/2000 | Cuschieri et al. | |
| 6,083,242 A | 7/2000 | Cook | |
| 6,086,600 A | 7/2000 | Kortenbach | |
| 6,099,551 A | 8/2000 | Gabbay | |
| 6,102,271 A | 8/2000 | Longo et al. | |
| 6,126,058 A | 10/2000 | Adams et al. | |
| 6,165,188 A * | 12/2000 | Saadat et al. | 606/159 |
| 6,171,330 B1 | 1/2001 | Benchetrit | |
| 6,197,042 B1 | 3/2001 | Ginn et al. | |
| 6,241,139 B1 | 6/2001 | Milliman et al. | |
| 6,250,532 B1 | 6/2001 | Green et al. | |
| 6,264,086 B1 | 7/2001 | McGuckin, Jr. | |
| 6,264,087 B1 | 7/2001 | Whitman | |
| 6,273,897 B1 | 8/2001 | Dalessandro et al. | |
| 6,315,184 B1 | 11/2001 | Whitman | |
| 6,387,113 B1 | 5/2002 | Hawkins et al. | |
| RE37,814 E | 8/2002 | Allgeyer | |
| 6,436,107 B1 | 8/2002 | Wang et al. | |
| 6,443,973 B1 | 9/2002 | Whitman | |
| 6,488,196 B1 | 12/2002 | Fenton, Jr. | |
| 6,488,197 B1 | 12/2002 | Whitman | |
| 6,491,201 B1 | 12/2002 | Whitman | |
| 6,494,896 B1 | 12/2002 | D'Alessio et al. | |
| 6,505,768 B2 | 1/2003 | Whitman | |
| 6,517,565 B1 | 2/2003 | Whitman et al. | |
| 6,569,171 B2 | 5/2003 | DeGuillebon et al. | |
| 6,601,749 B2 | 8/2003 | Sullivan et al. | |
| 6,616,686 B2 | 9/2003 | Coleman et al. | |
| 6,629,630 B2 | 10/2003 | Adams | |
| 6,629,988 B2 | 10/2003 | Weadock | |
| RE38,335 E | 11/2003 | Aust et al. | |
| 6,644,532 B2 | 11/2003 | Green et al. | |
| 6,681,979 B2 | 1/2004 | Whitman | |
| 6,685,727 B2 | 2/2004 | Fisher et al. | |
| 6,695,199 B2 | 2/2004 | Whitman | |
| 6,698,643 B2 | 3/2004 | Whitman | |
| 6,716,233 B1 | 4/2004 | Whitman | |
| 6,752,816 B2 | 6/2004 | Culp et al. | |

(56) References Cited

U.S. PATENT DOCUMENTS

| | | |
|---|---|---|
| 6,755,338 B2 | 6/2004 | Hahnen et al. |
| 6,767,356 B2 | 7/2004 | Kanner et al. |
| 6,773,438 B1 | 8/2004 | Knodel et al. |
| 6,786,382 B1 | 9/2004 | Hoffman |
| 6,805,273 B2 | 10/2004 | Bilotti et al. |
| 6,830,174 B2 | 12/2004 | Hillstead et al. |
| 6,835,199 B2 | 12/2004 | McGuckin, Jr. et al. |
| RE38,708 E | 3/2005 | Bolanos et al. |
| 6,874,669 B2 | 4/2005 | Adams et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,922 B2 | 12/2005 | Bilotti et al. |
| 6,981,628 B2 | 1/2006 | Wales |
| 7,000,818 B2 | 2/2006 | Shelton, IV et al. |
| 7,008,435 B2 | 3/2006 | Cummins |
| 7,018,390 B2 | 3/2006 | Turovskiy et al. |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,056,330 B2 | 6/2006 | Gayton |
| 7,077,856 B2 | 7/2006 | Whitman |
| 7,090,684 B2 | 8/2006 | McGuckin, Jr. et al. |
| 7,108,709 B2 | 9/2006 | Cummins |
| 7,111,769 B2 | 9/2006 | Wales et al. |
| 7,114,642 B2 | 10/2006 | Whitman |
| 7,118,582 B1 | 10/2006 | Wang et al. |
| 7,140,527 B2 | 11/2006 | Ehrenfels et al. |
| 7,159,750 B2 | 1/2007 | Racenet et al. |
| 7,188,758 B2 | 3/2007 | Viola et al. |
| 7,210,609 B2 | 5/2007 | Leiboff et al. |
| 7,213,736 B2 | 5/2007 | Wales et al. |
| 7,220,272 B2 | 5/2007 | Weadock |
| 7,235,089 B1 | 6/2007 | McGuckin, Jr. |
| 7,238,195 B2 | 7/2007 | Viola |
| 7,246,734 B2 | 7/2007 | Shelton, IV |
| 7,278,563 B1 | 10/2007 | Green |
| 7,297,149 B2 | 11/2007 | Vitali et al. |
| 7,303,106 B2 | 12/2007 | Milliman et al. |
| 7,328,828 B2 | 2/2008 | Ortiz et al. |
| 7,343,920 B2 | 3/2008 | Toby et al. |
| 7,354,447 B2 | 4/2008 | Shelton, IV et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,404,508 B2 | 7/2008 | Smith et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,730 B2 | 10/2008 | Viola |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,455,208 B2 | 11/2008 | Wales et al. |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,481,347 B2 | 1/2009 | Roy |
| 7,490,749 B2 | 2/2009 | Schall et al. |
| 7,494,039 B2 | 2/2009 | Racenet et al. |
| 7,500,979 B2 | 3/2009 | Hueil et al. |
| 7,506,791 B2 | 3/2009 | Omaits et al. |
| 7,510,107 B2 | 3/2009 | Timm et al. |
| 7,546,940 B2 | 6/2009 | Milliman et al. |
| 7,549,564 B2 | 6/2009 | Boudreaux |
| 7,559,450 B2 | 7/2009 | Wales et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,631,793 B2 | 12/2009 | Rethy et al. |
| 7,644,848 B2 | 1/2010 | Swayze et al. |
| 7,658,311 B2 | 2/2010 | Boudreaux |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,699,204 B2 | 4/2010 | Viola |
| 7,717,312 B2 | 5/2010 | Beetel |
| 7,721,931 B2 | 5/2010 | Shelton, IV et al. |
| 7,721,934 B2 | 5/2010 | Shelton, IV et al. |
| 7,721,936 B2 | 5/2010 | Shalton, IV et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,210 B2 | 8/2010 | Shelton, IV et al. |
| 7,770,775 B2 | 8/2010 | Shelton, IV et al. |
| 7,780,054 B2 | 8/2010 | Wales |
| 7,784,662 B2 | 8/2010 | Wales et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,692 B2 | 10/2010 | Hall et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,832,408 B2 | 11/2010 | Shelton, IV et al. |
| 7,832,612 B2 | 11/2010 | Baxter, III et al. |
| 7,837,080 B2 | 11/2010 | Schwemberger |
| 7,845,537 B2 | 12/2010 | Shelton, IV et al. |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 8,409,079 B2 * | 4/2013 | Okamoto et al. ............. 600/146 |
| 2003/0093103 A1 | 5/2003 | Malackowski et al. |
| 2003/0105478 A1 | 6/2003 | Whitman et al. |
| 2003/0130677 A1 | 7/2003 | Whitman et al. |
| 2004/0006372 A1 | 1/2004 | Racenet et al. |
| 2004/0034369 A1 | 2/2004 | Sauer et al. |
| 2004/0044364 A1 | 3/2004 | DeVries et al. |
| 2004/0094597 A1 | 5/2004 | Whitman et al. |
| 2004/0167572 A1 | 8/2004 | Roth et al. |
| 2004/0222268 A1 | 11/2004 | Bilotti et al. |
| 2004/0243151 A1 | 12/2004 | Demmy et al. |
| 2004/0254608 A1 | 12/2004 | Huitema et al. |
| 2005/0059997 A1 | 3/2005 | Bauman et al. |
| 2005/0096683 A1 | 5/2005 | Ellins et al. |
| 2005/0096694 A1 * | 5/2005 | Lee ............................ 606/205 |
| 2005/0103819 A1 | 5/2005 | Racenet et al. |
| 2005/0119669 A1 | 6/2005 | Demmy |
| 2005/0125009 A1 | 6/2005 | Perry et al. |
| 2005/0143759 A1 | 6/2005 | Kelly |
| 2005/0184121 A1 | 8/2005 | Heinrich |
| 2005/0187576 A1 | 8/2005 | Whitman et al. |

(56) References Cited

U.S. PATENT DOCUMENTS

| | | |
|---|---|---|
| 2005/0192609 A1 | 9/2005 | Whitman et al. |
| 2005/0192628 A1 | 9/2005 | Viola |
| 2005/0216055 A1 | 9/2005 | Scirica et al. |
| 2005/0240222 A1 | 10/2005 | Shipp |
| 2005/0274768 A1 | 12/2005 | Cummins et al. |
| 2006/0011699 A1 | 1/2006 | Olson et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0085033 A1 | 4/2006 | Criscuolo et al. |
| 2006/0100643 A1 | 5/2006 | Laufer et al. |
| 2006/0122636 A1 | 6/2006 | Bailly et al. |
| 2006/0226196 A1 | 10/2006 | Hueil et al. |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0073341 A1 | 3/2007 | Smith |
| 2007/0102472 A1 | 5/2007 | Shelton, IV |
| 2007/0106317 A1 | 5/2007 | Shelton, IV et al. |
| 2007/0114261 A1 | 5/2007 | Ortiz et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0246505 A1 | 10/2007 | Pace-Floridia et al. |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082125 A1 | 4/2008 | Murray et al. |
| 2008/0082126 A1 | 4/2008 | Murray et al. |
| 2008/0140115 A1 | 6/2008 | Stopek |
| 2008/0167522 A1 | 7/2008 | Giordano et al. |
| 2008/0167644 A1 | 7/2008 | Shelton et al. |
| 2008/0167671 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0210738 A1 | 9/2008 | Shelton et al. |
| 2008/0237296 A1 | 10/2008 | Boudreaux et al. |
| 2008/0251568 A1 | 10/2008 | Zemlok et al. |
| 2008/0283570 A1 | 11/2008 | Boyden et al. |
| 2008/0296346 A1 | 12/2008 | Shelton, IV et al. |
| 2008/0300580 A1 | 12/2008 | Shelton, IV et al. |
| 2008/0300613 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0314957 A1 | 12/2008 | Boudreaux |
| 2008/0314960 A1 | 12/2008 | Marczyk et al. |
| 2009/0001121 A1 | 1/2009 | Hess et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0057369 A1 | 3/2009 | Smith et al. |
| 2009/0076534 A1 | 3/2009 | Shelton, IV et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0242610 A1 | 10/2009 | Shelton, IV et al. |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0289096 A1 | 11/2009 | Shelton, IV et al. |
| 2010/0032470 A1 | 2/2010 | Hess et al. |
| 2010/0065605 A1 | 3/2010 | Shelton, IV et al. |
| 2010/0069942 A1 | 3/2010 | Shelton, IV |
| 2010/0072252 A1 | 3/2010 | Baxter, III et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089974 A1 | 4/2010 | Shelton, IV |
| 2010/0096435 A1 | 4/2010 | Fuchs et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0179382 A1* | 7/2010 | Shelton et al. .............. 600/104 |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0237132 A1 | 9/2010 | Measamer et al. |
| 2010/0243709 A1 | 9/2010 | Hess et al. |
| 2010/0264193 A1 | 10/2010 | Huang et al. |
| 2010/0264194 A1 | 10/2010 | Huang et al. |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308100 A1 | 12/2010 | Boudreaux |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |

FOREIGN PATENT DOCUMENTS

| | | |
|---|---|---|
| CA | 2514274 A1 | 1/2006 |
| DE | 273689 C | 5/1914 |
| DE | 1775926 A | 1/1972 |
| DE | 3210466 A1 | 9/1983 |
| DE | 9412228 U | 9/1994 |
| DE | 19924311 A1 | 11/2000 |
| DE | 69328576 T2 | 1/2001 |
| DE | 20112837 U1 | 10/2001 |
| DE | 20121753 U1 | 4/2003 |
| DE | 10314072 A1 | 10/2004 |
| EP | 0122046 A1 | 10/1984 |
| EP | 0070230 B1 | 10/1985 |
| EP | 0033548 B1 | 5/1986 |
| EP | 0276104 A2 | 7/1988 |
| EP | 0639349 A2 | 2/1994 |

(56) References Cited

FOREIGN PATENT DOCUMENTS

| | | |
|---|---|---|
| EP | 0324636 B1 | 3/1994 |
| EP | 0593920 A1 | 4/1994 |
| EP | 0600182 A2 | 6/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0699418 A1 | 3/1996 |
| EP | 0702937 A1 | 3/1996 |
| EP | 0705571 A1 | 4/1996 |
| EP | 0484677 B2 | 6/1996 |
| EP | 0541987 B1 | 7/1996 |
| EP | 0667119 B1 | 7/1996 |
| EP | 0770355 A1 | 5/1997 |
| EP | 0503662 B1 | 6/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0676173 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0760230 B1 | 2/1999 |
| EP | 0537572 B1 | 6/1999 |
| EP | 0552050 B1 | 5/2000 |
| EP | 1090592 A1 | 4/2001 |
| EP | 1256318 B1 | 5/2001 |
| EP | 0908152 B1 | 1/2002 |
| EP | 0872213 B1 | 5/2002 |
| EP | 1238634 A2 | 9/2002 |
| EP | 0656188 B1 | 1/2003 |
| EP | 0829235 B1 | 6/2003 |
| EP | 0813843 B1 | 10/2003 |
| EP | 0741996 B1 | 2/2004 |
| EP | 0705570 B1 | 4/2004 |
| EP | 1086713 B1 | 5/2004 |
| EP | 1426012 A1 | 6/2004 |
| EP | 0888749 B1 | 9/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 1520521 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1157666 B1 | 9/2005 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1652481 A2 | 5/2006 |
| EP | 1382303 B1 | 6/2006 |
| EP | 1045672 B1 | 8/2006 |
| EP | 1617768 B1 | 8/2006 |
| EP | 1702567 A2 | 9/2006 |
| EP | 1129665 B1 | 11/2006 |
| EP | 1400206 B1 | 11/2006 |
| EP | 1256317 B1 | 12/2006 |
| EP | 1728473 A1 | 12/2006 |
| EP | 1728475 A2 | 12/2006 |
| EP | 1479346 B1 | 1/2007 |
| EP | 1484024 B1 | 1/2007 |
| EP | 1754445 A2 | 2/2007 |
| EP | 1759812 A1 | 3/2007 |
| EP | 1769756 A1 | 4/2007 |
| EP | 1769758 A1 | 4/2007 |
| EP | 1785097 A2 | 5/2007 |
| EP | 1790293 A2 | 5/2007 |
| EP | 1800610 A1 | 6/2007 |
| EP | 1300117 B1 | 8/2007 |
| EP | 1813199 A1 | 8/2007 |
| EP | 1813201 A1 | 8/2007 |
| EP | 1813203 A2 | 8/2007 |
| EP | 1813207 A1 | 8/2007 |
| EP | 1813209 A1 | 8/2007 |
| EP | 1839596 A2 | 10/2007 |
| EP | 1402821 B1 | 12/2007 |
| EP | 1872727 A1 | 1/2008 |
| EP | 1897502 A1 | 3/2008 |
| EP | 1702568 B1 | 7/2008 |
| EP | 1970014 A1 | 9/2008 |
| EP | 1980213 A2 | 10/2008 |
| EP | 1759645 B1 | 11/2008 |
| EP | 1693008 B1 | 12/2008 |
| EP | 1759640 B1 | 12/2008 |
| EP | 2000102 A2 | 12/2008 |
| EP | 1749486 B1 | 3/2009 |
| EP | 2090256 A2 | 8/2009 |
| EP | 1813206 B1 | 4/2010 |
| EP | 1769754 B1 | 6/2010 |
| EP | 1702570 B1 | 10/2010 |
| FR | 999646 A | 2/1952 |
| FR | 1112936 A | 3/1956 |
| FR | 2765794 A | 1/1999 |
| GB | 939929 A | 10/1963 |
| GB | 1210522 A | 10/1970 |
| GB | 2336214 A | 10/1999 |
| JP | 6007357 A | 1/1994 |
| JP | 7051273 A | 2/1995 |
| JP | 8033641 A | 2/1996 |
| JP | 8229050 A | 9/1996 |
| JP | 2000287987 A | 10/2000 |
| JP | 2001286477 A | 10/2001 |
| JP | 2002369820 A | 12/2002 |
| JP | 2005505322 T | 2/2005 |
| JP | 2005103293 A | 4/2005 |
| RU | 2187249 C2 | 8/2002 |
| RU | 2225170 C2 | 3/2004 |
| SU | 1377053 A1 | 2/1988 |
| SU | 1561964 A1 | 5/1990 |
| SU | 1722476 A1 | 3/1992 |
| WO | WO 93/08755 A1 | 5/1993 |
| WO | WO 95/18572 A1 | 7/1995 |
| WO | WO 95/23557 A1 | 9/1995 |
| WO | WO 95/29639 A1 | 11/1995 |
| WO | WO 96/22055 A1 | 7/1996 |
| WO | WO 96/35464 A1 | 11/1996 |
| WO | WO 97/34533 A1 | 9/1997 |
| WO | WO 97/39688 A2 | 10/1997 |
| WO | WO 98/17180 A1 | 4/1998 |
| WO | WO 98/30153 A1 | 7/1998 |
| WO | WO 99/12483 A1 | 3/1999 |
| WO | WO 99/15086 A1 | 4/1999 |
| WO | WO 99/34744 A1 | 7/1999 |
| WO | WO 99/45849 A1 | 9/1999 |
| WO | WO 00/24322 A1 | 5/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/05702 A1 | 1/2001 |
| WO | WO 01/10482 A1 | 2/2001 |
| WO | WO 01/54594 A1 | 8/2001 |
| WO | WO 01/62158 A2 | 8/2001 |
| WO | WO 01/62162 A1 | 8/2001 |
| WO | WO 01/62164 A2 | 8/2001 |
| WO | WO 01/91646 A1 | 12/2001 |
| WO | WO 02/07608 A2 | 1/2002 |
| WO | WO 02/07618 A1 | 1/2002 |

(56) References Cited

FOREIGN PATENT DOCUMENTS

| | | |
|---|---|---|
| WO | WO 02/17799 A1 | 3/2002 |
| WO | WO 02/19920 A1 | 3/2002 |
| WO | WO 02/30297 A2 | 4/2002 |
| WO | WO 02/32322 A2 | 4/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/020106 A2 | 3/2003 |
| WO | WO 03/020139 A2 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/078892 A1 | 8/2005 |
| WO | WO 2005/096954 A2 | 10/2005 |
| WO | WO 2005/112808 A1 | 12/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/115958 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/039270 A1 | 4/2008 |
| WO | WO 2008/045383 A2 | 4/2008 |
| WO | WO 2008/109125 A1 | 9/2008 |

OTHER PUBLICATIONS

Extended European Search Report, Application No. 06255736.8, dated Dec. 27, 2007 (10 pages).
Notification of First Office Action from the Patent Office of the People's Republic of China, Application No. 200610136656.1, dated Jul. 24, 2009 (5 pages).
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, 2000, 3 pages.
"Biomedical Coatings," Fort Wayne Metals, Research Products Corporation, obtained online at www.fwmetals.com on Jun. 21, 2010 (1 page).

* cited by examiner

HYDRAULICALLY AND ELECTRICALLY ACTUATED ARTICULATION JOINTS FOR SURGICAL INSTRUMENTS

CROSS-REFERENCE TO RELATED APPLICATIONS

This non-provisional application for patent is a divisional patent application of U.S. patent application Ser. No. 11/270,866, filed Nov. 9, 2005, now abandoned, the disclosure of which is herein incorporated by reference in its entirety.

FIELD OF THE INVENTION

The present invention relates in general to surgical instruments that are suitable for endoscopically inserting an end effector (e.g., endocutter, grasper, cutter, staplers clip applier, access device, drug/gene therapy delivery device, an energy device using ultrasound, RF, laser, etc.) and, more particularly, to endocutters with articulating end effectors.

BACKGROUND OF THE INVENTION

Endoscopic surgical instruments are often preferred over traditional open surgical devices since a smaller incision tends to reduce the post-operative recovery time and complications. Generally, these endoscopic surgical instruments include an "end effector", a handle assembly and a long shaft that extends between the end effector and the handle assembly. The end effector is the portion of the instrument configured to engage the tissue in various ways to achieve a desired diagnostic or therapeutic effect (e.g., endocutter, grasper, cutter, staplers, clip applier, access device, drug/gene therapy delivery device, and energy device using ultrasound, RF, laser, etc.). The end effector and the shaft portion are sized to be inserted through a trocar placed into the patient. The elongated shaft portion enables the end effector to be inserted to a desired depth and also facilitates some rotation of the end effector to position it within the patient. With judicious placement of the trocar and use of graspers, for instance, through another trocar, often this amount of positioning is sufficient. Surgical stapling and severing instruments, such as those described in U.S. Pat. No. 5,465,895, are an example of an endoscopic surgical instrument that successfully positions an end effector by insertion and rotation.

Depending upon the nature of the operation, it may be desirable to further adjust the positioning of the end effector of an endoscopic surgical instrument. In particular, it is often desirable to orient the end effector at an angle relative to the longitudinal axis of the shaft of the instrument. The transverse or non-axial movement of the end effector relative to the instrument shaft is often conventionally referred to as "articulation". This articulated positioning permits the clinician to more easily engage tissue in some instances, such as behind an organ. In addition, articulated positioning advantageously allows an endoscope to be positioned behind the end effector without being blocked by the instrument shaft.

Approaches to articulating a surgical stapling and severing instrument tend to be complicated by integrating control of the articulation along with the control of closing the end effector to clamp tissue and fire the end effector (i.e., stapling and severing) within the small diameter constraints of an endoscopic instrument. Generally, the three control motions are all transferred through the shaft as longitudinal translations. For instance, U.S. Pat. No. 5,673,840 discloses an accordion-like articulation mechanism ("flex-neck") that is articulated by selectively drawing back one of two connecting rods through the implement shaft, each rod offset respectively on opposite sides of the shaft centerline. The connecting rods ratchet through a series of discrete positions.

Another example of longitudinal control of an articulation mechanism is U.S. Pat. No. 5,865,361 that includes an articulation link offset from a camming pivot such that pushing or pulling longitudinal translation of the articulation link effects articulation to a respective side. Similarly, U.S. Pat. No. 5,797,537 discloses a similar rod passing through the shaft to effect articulation. Still other examples of articulatable surgical stapling devices are disclosed in U.S. Pat. Nos. 6,250,532 and 6,644,532.

Due to the types end effector firing systems commonly employed, the actuator arrangements for articulating the end effector must often generate high amounts of torque to bend the firing structure. This problem is exacerbated by the lack of available space for accommodating actuating devices that are large enough to generate those required forces.

Consequently, a significant need exists for an articulating surgical instrument that incorporates an articulation mechanism that can generate the torque necessary to selectively articulate the end effector thereof in a desired manner.

BRIEF SUMMARY OF THE INVENTION

In accordance with another non-limiting embodiment of the present invention there is provided a surgical instrument that comprises a handle assembly and a proximal tube segment that is attached to the handle assembly. The surgical instrument further comprises a distal tube segment that is attached to the proximal tube segment by an articulating joint assembly. In one non-limiting embodiment, the articulating joint assembly comprises a ball member non-movably coupled to an end of one of the proximal and distal tube segments and being rotatably received in a corresponding socket in an end of the other of the proximal tube segment and distal tube segment. At least one flexible cable is attached to a motor. The flexible cable may have a series of worm gear teeth thereon that are arranged to drivingly engage a corresponding passageway formed in the ball member or socket for retaining a portion of the ball member in the socket and, upon selective rotation thereof, articulate the distal tube segment relative to the proximal tube segment. A surgical implement may be attached to the distal tube segment.

In accordance with another embodiment of the present invention there is provided a surgical instrument that comprises a handle assembly and a proximal tube segment that is attached to the handle assembly. The surgical instrument may further comprise a distal tube segment that is attached to the proximal tube segment by an articulating joint assembly. In one non-limiting embodiment, the articulating joint assembly may comprise a ball member that is non-movably coupled to a distal end of one of the proximal and distal tube segments. The ball member may be rotatably received in a corresponding socket in an end of the other of the proximal tube segment and the distal tube segment. At least one rotary driven flexible cable may be arranged to drivingly engage a corresponding portion of the ball member or socket to retain the ball member in the socket and, upon selective rotation thereof, articulate the distal tube segment relative to the proximal tube segment. A surgical implement may be attached to the distal tube segment.

In accordance with another non-limiting embodiment of the present invention there is provided a surgical instrument that comprises a handle assembly and a proximal tube segment that is attached to the handle assembly. The surgical instrument further comprises a distal tube segment that is attached to the proximal tube segment by an articulating joint assembly. In one non-limiting embodiment, the articulating joint assembly comprises a disc-like member non-movably coupled to an end of one of the proximal and distal tube segments and being rotatably received in a corresponding socket in an end of the other of the proximal tube segment and distal tube segment. At least one rotary driven flexible cable may be arranged to drivingly engage a corresponding portion of the disc-like member or socket for retaining a portion of the disc-like member in the socket and, upon selective rotation, to articulate the distal tube segment relative to the proximal tube segment. A surgical implement may be attached to the distal tube segment.

One feature of various embodiments of the present invention is to provide an articulation joint that enables the proximal and distal tube segments to be coaxially aligned for insertion through a passageway in a trocar and then articulated relative to each other after the joint has passed through the trocar. Accordingly, various embodiments of the invention provide solutions to the shortcomings of other articulated surgical instruments that are designed to be passed through a trocar or similar structure. Those of ordinary skill in the art will readily appreciate, however, that these and other details, features and advantages will become further apparent as the following Detailed Description proceeds.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain various principles of the various embodiments of the present invention.

DETAILED DESCRIPTION OF THE INVENTION

Figure 1:
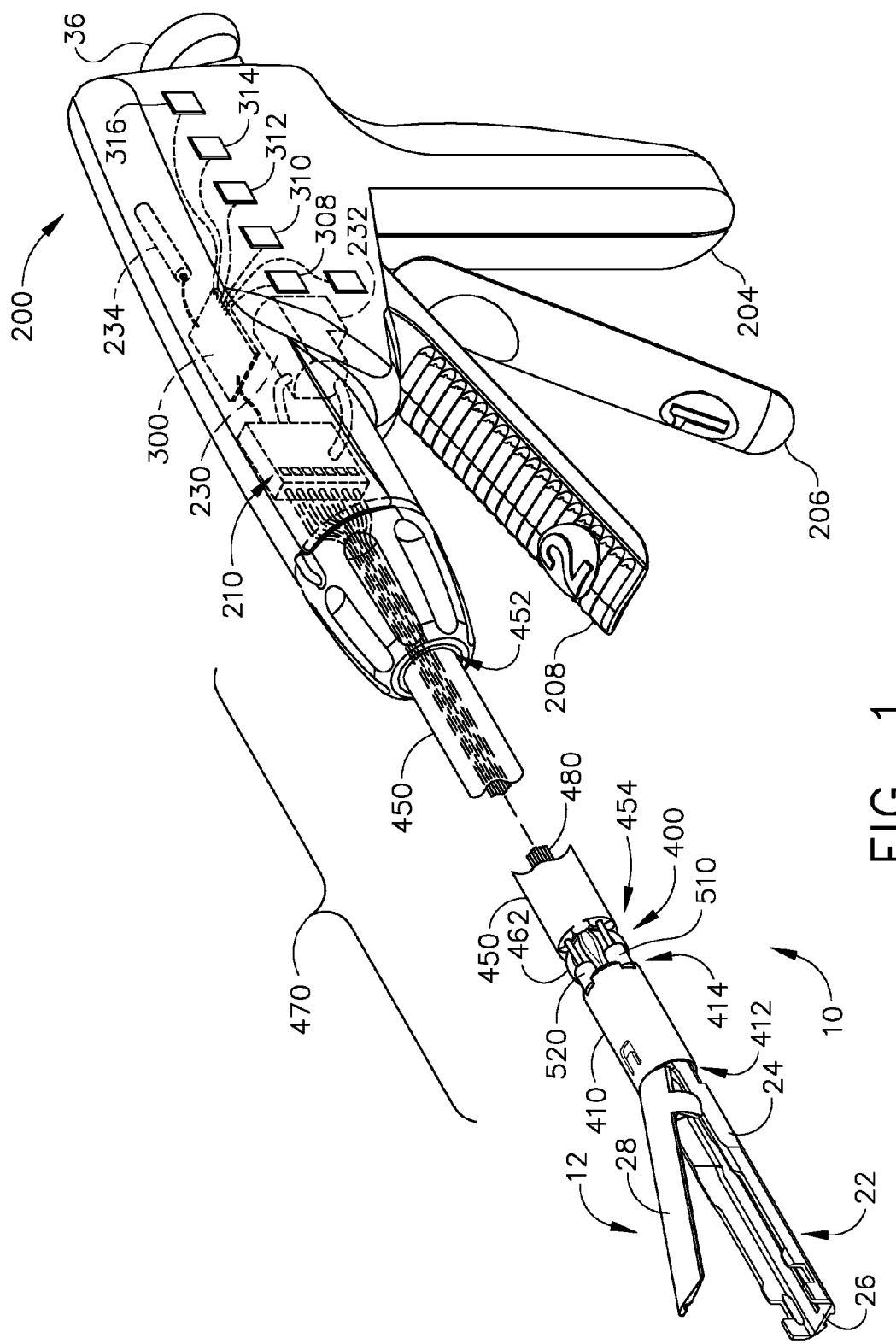
FIG. 1 is a partial perspective view of one non-limiting embodiment of a moment arm extension arrangement employed in connection with a hydraulically operated endocutter with the tube segments thereof in a first substantially coaxially aligned position.
Figure 2:
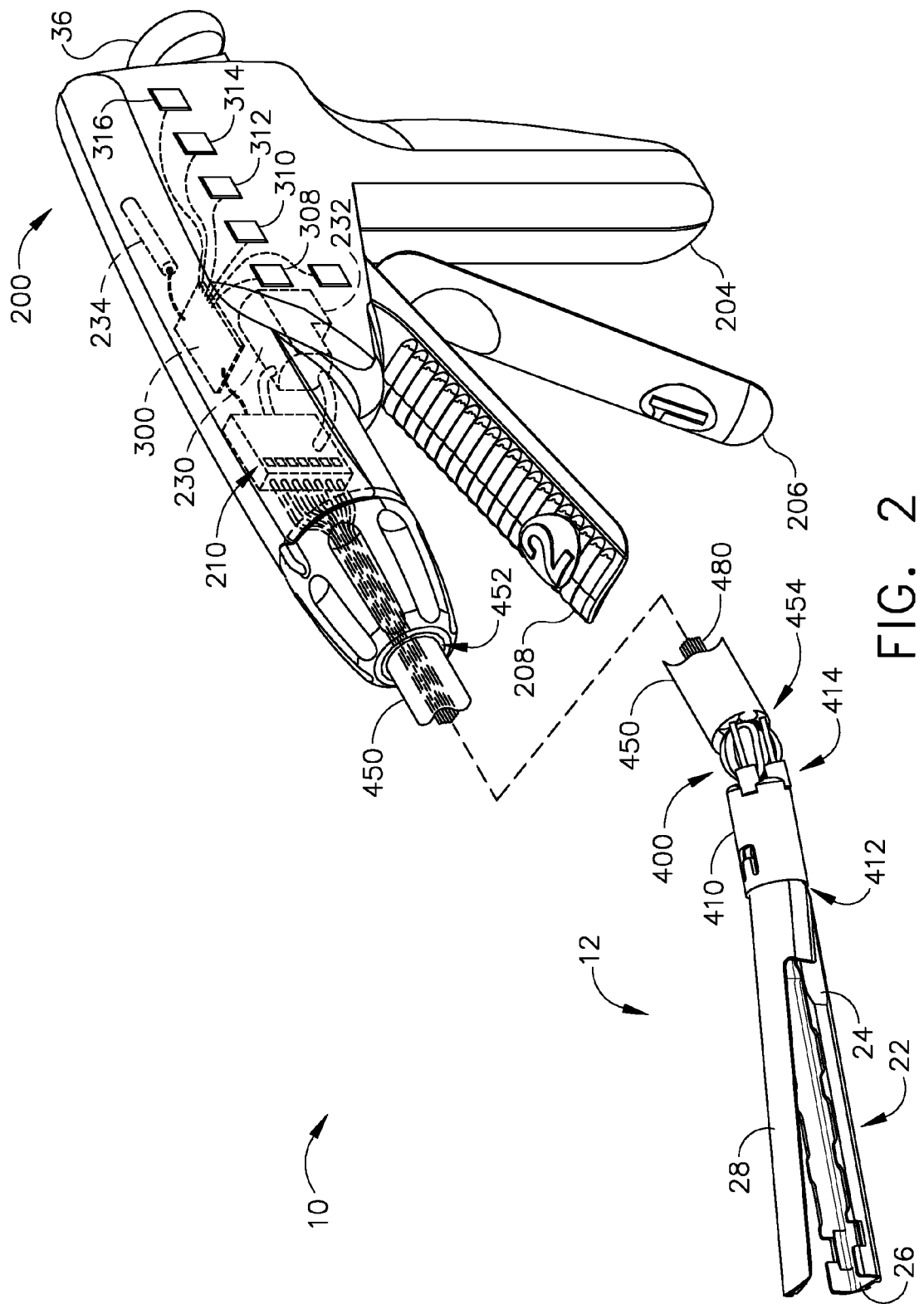
FIG. 2 is another perspective view of the moment arm extension arrangement and endocutter of FIG. 1 with the tube segments articulated at an angle relative to each other.

Turning to the Figures, wherein like numerals denote like components throughout the several views, FIGS. 1 and 2 depict one embodiment of a surgical instrument 10 that is capable of practicing the unique benefits of the present invention. As can be seen in FIGS. 1 and 2, the instrument 10 includes a handle assembly 200 and a surgical implement portion 12. As used herein, the term "surgical implement" refers to a component or set of components configured to engage tissue to accomplish a surgical task. Examples of surgical implements include, but are not limited to: endocutters, graspers, clamps, cutters, staplers, clip appliers, probes or access devices, drug/gene therapy delivery devices, energy devices such as ultrasound, RF, or laser devices, etc.

In the non-limiting embodiment depicted in the Figures, the surgical instrument 10 includes a hydraulically actuated end effector 22 and handle arrangement 200 of the type disclosed in the U.S. patent application Ser. No. 11/270,217, entitled "SURGICAL INSTRUMENT HAVING A HYDRAULICALLY ACTUATED END EFFECTOR" to Frederick E. Shelton IV and Jerome R. Morgan, that was filed on even date herewith and which is commonly owned with the present application and which the disclosure thereof is hereby incorporated by reference in its entirety. As the present Detailed Description proceeds, however, the skilled artisan will readily appreciate that the unique and novel features of the various embodiments of the present invention may also be employed in connection with electrically actuated or pneumatically actuated end effectors. Thus, the various embodiments of the present invention may be advantageously employed in connection with a variety of surgical implements other than the exemplary embodiment depicted in the Figures without departing from the spirit and scope of the present invention. Accordingly, the scope of protection afforded to the various embodiments of the present invention should not be limited to use only with the specific type of surgical implements specifically described herein.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Figure 3:
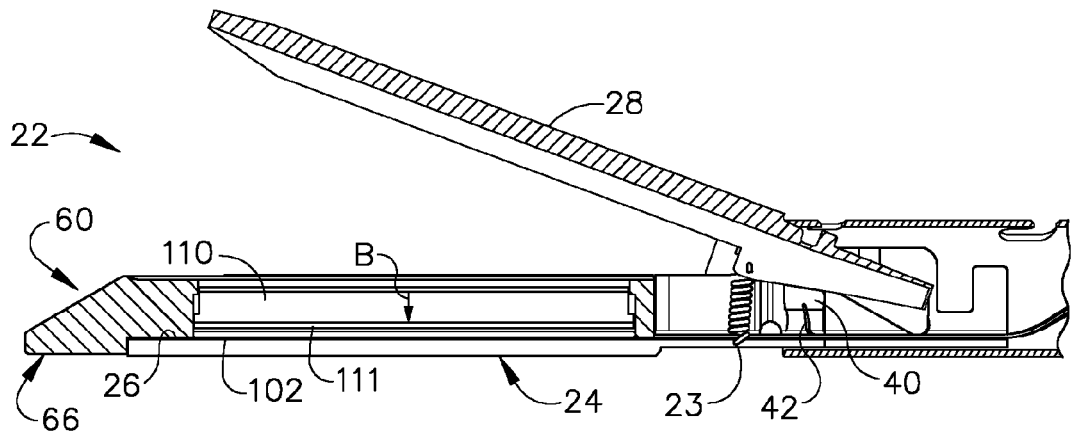
FIG. 3 is a partial cross-sectional view of an end effector employed in the endocutter depicted in FIGS. 1 and 2 with the anvil thereof in an open or unclamped position with some of the elements thereof omitted for clarity.
Figure 4:
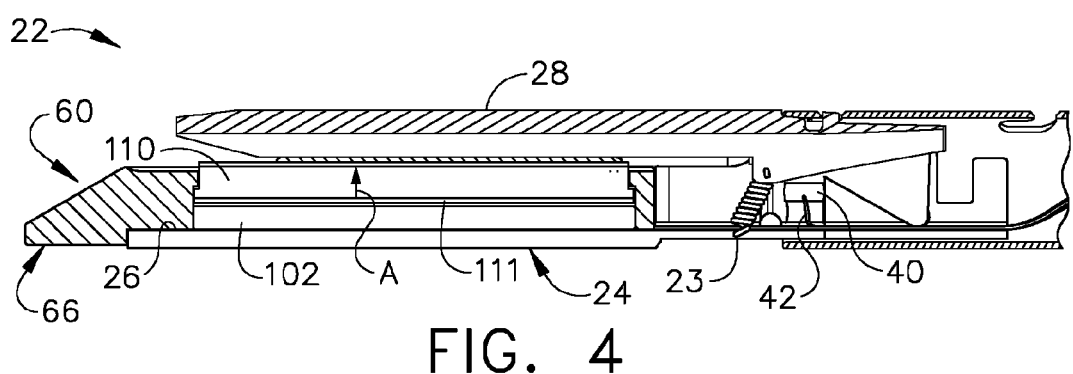
FIG. 4 is another cross-sectional view of the end effector of FIG. 3 in a closed or clamped position with the cutting bar in an extended position.
Figure 5:
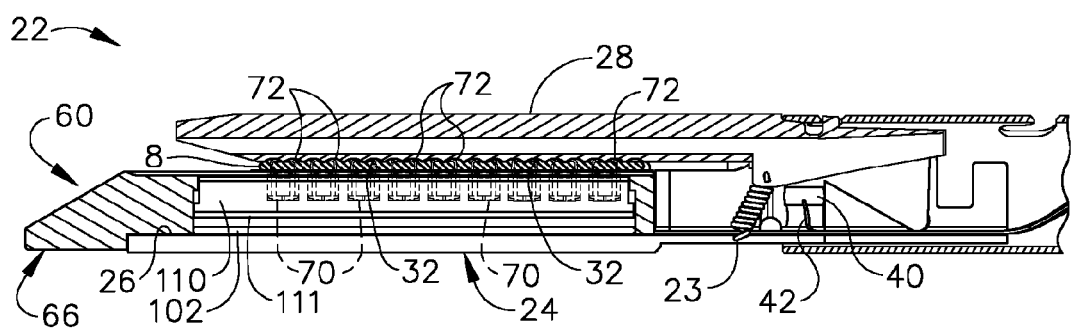
FIG. 5 is another cross-sectional view of the end effector of FIGS. 3 and 4 showing tissue after being cut and stapled therein.
Figure 10:
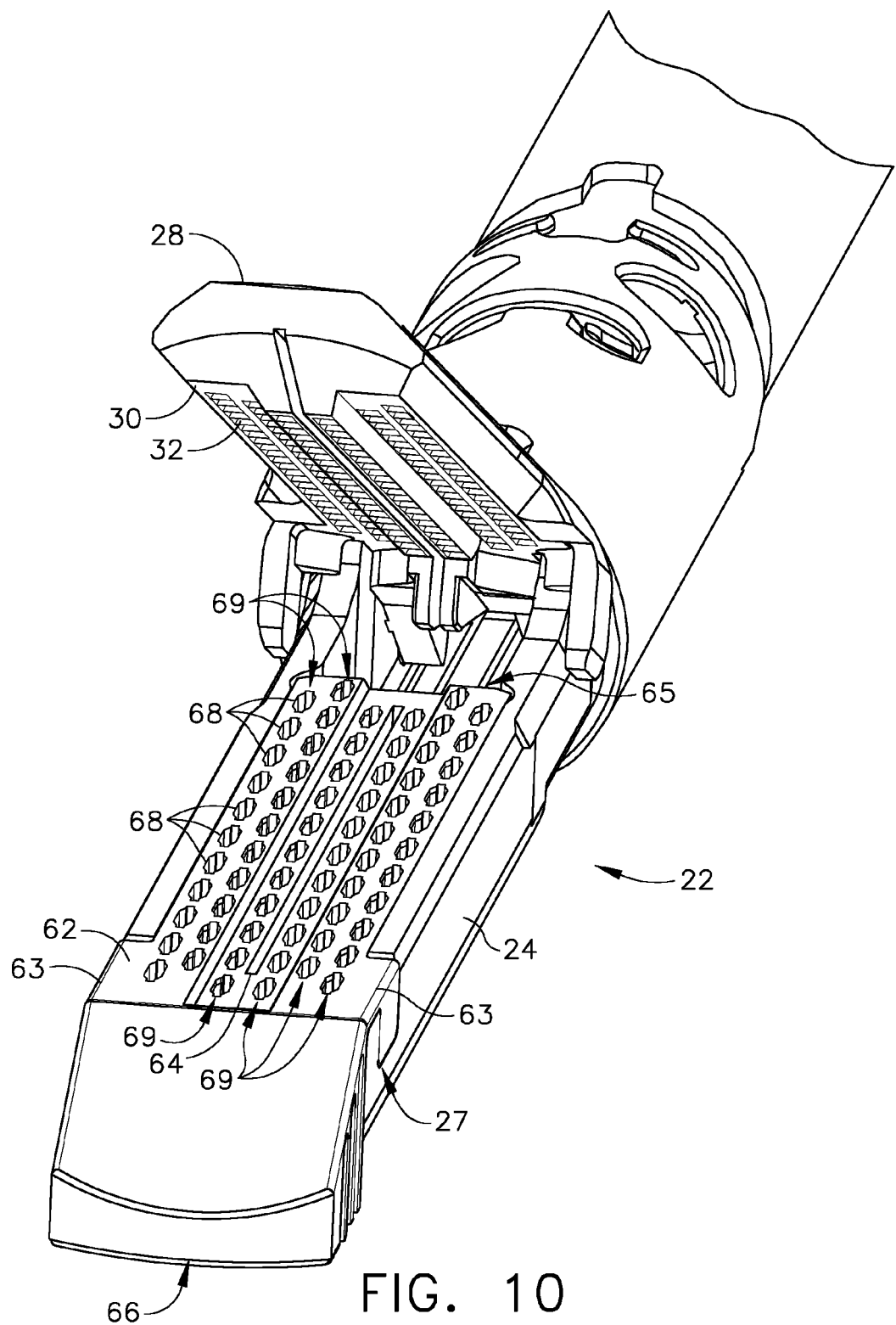
FIG. 10 is a perspective view of a cartridge installed in an end effector with the anvil thereof in an open or unclamped position.

FIGS. 3-10 show views of one type of end effector 22 configured to perform clamping, severing and stapling of tissue according to various embodiments the present invention. In one embodiment, the end effector 22 has a body portion 24 that is provided with an elongate channel 26 for receiving a staple cartridge 60 therein. An anvil 28 is coupled to the body portion 24 and is capable of being selectively pivoted toward and away from cartridge 60 mounted in the elongate channel 26. FIGS. 3 and 10 illustrate the anvil 28 in an open position and FIGS. 4 and 5 illustrate the anvil 28 in a closed position. The anvil 28 may be closed hydraulically and returned to its open position by an energy storing device such as a spring 23. As can be seen in FIGS. 3-5, an actuation bladder 40 may be strategically mounted below a portion of the anvil 28 such that when the bladder 40 is inflated with a pressurized fluid or air, it biases the anvil 28 to its open position. A supply line 42 is coupled to the bladder 40 for supplying pressurized fluid from a reservoir 232 as will be described in further detail below. In alternative non-limiting embodiments, an additional hydraulic cylinder or cylinders may be advantageously employed to open and close the anvil. Still in other non-limiting embodiments, the anvil 28 may be opened and closed by slidable action of a distal tube segment 410 attached thereto.

One type of cartridge that may be used with such end effector is also depicted in FIGS. 3-10. The staple cartridge 60 has a cartridge body 62 that is divided by an elongated cutting slot 64 that extends from a proximal end 65 of the cartridge 60 toward a tapered outer tip 66. See FIG. 10. A plurality of staple-receiving channels 68 are formed within the staple cartridge body 64 and are arranged in spaced longitudinal rows 69 on each side of the elongated cutting slot 64. Positioned within the staple-receiving channels are staple drivers 70 that each support one or more staples 72 thereon. The staples 72 are advanced or "fired" by moving their respective drivers 70 in an upward direction toward the anvil 28.

FIG. 10 depicts a three dimensional view of the end effector 22 in an open position with a staple cartridge 60 installed in the elongate channel 26. On a lower surface 30 of the anvil 28, a plurality of staple-forming pockets 32 are arrayed to correspond to each staple receiving channel 68 in the cartridge body 62 when the cartridge 60 is installed in the end effector 22. More specifically, each forming pocket 32 in the anvil 28 may correspond to an individual staple 72 located within the staple cartridge 60. The staple cartridge 60 may be snap-fit into the elongate channel 26. For example, extension features 63 of the staple cartridge 60 engage recesses 27 (shown in FIG. 6) of the elongate channel 26.

Figure 6:
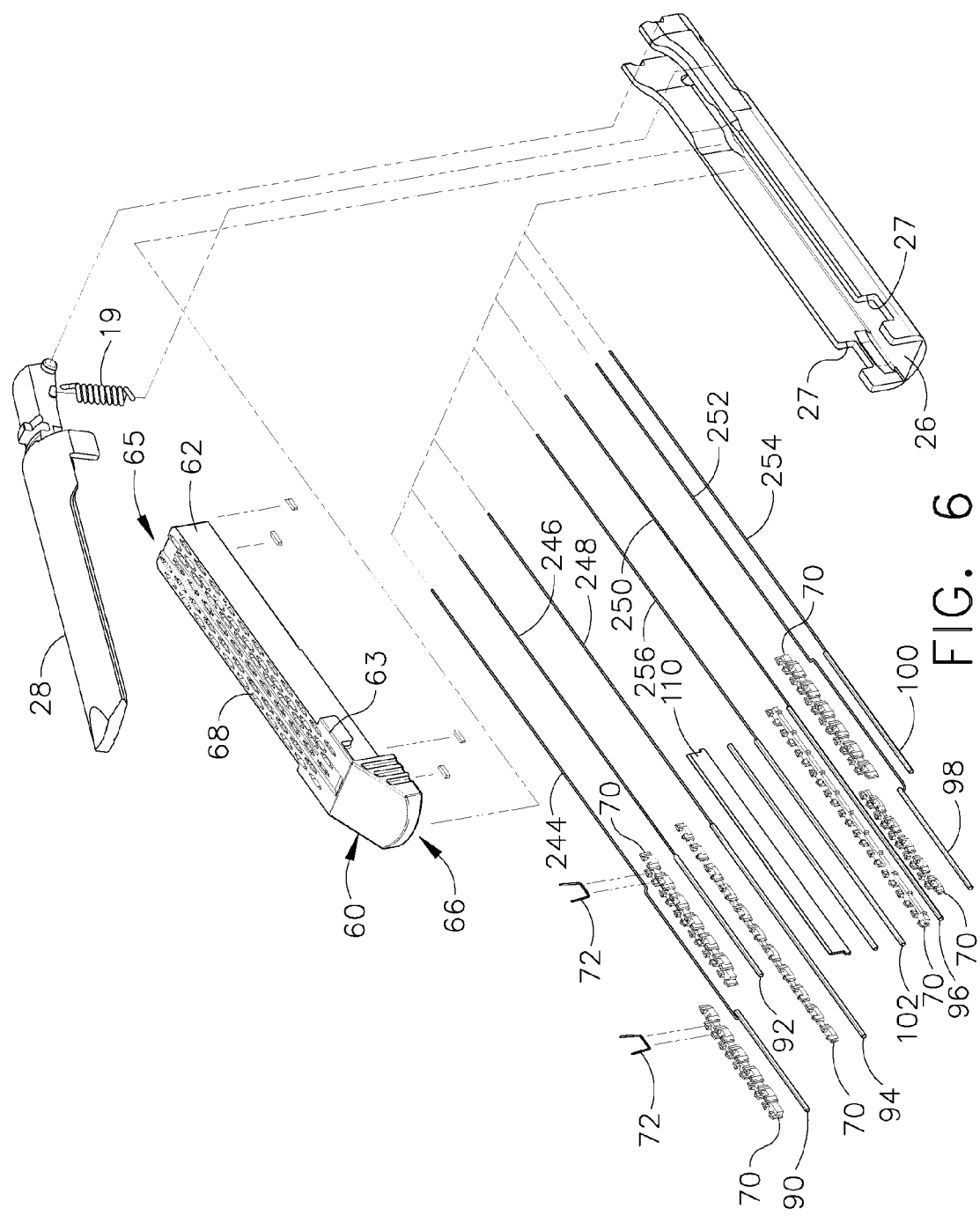
FIG. 6 is an exploded perspective view of the end effector depicted in FIGS. 1-5.
Figure 7:
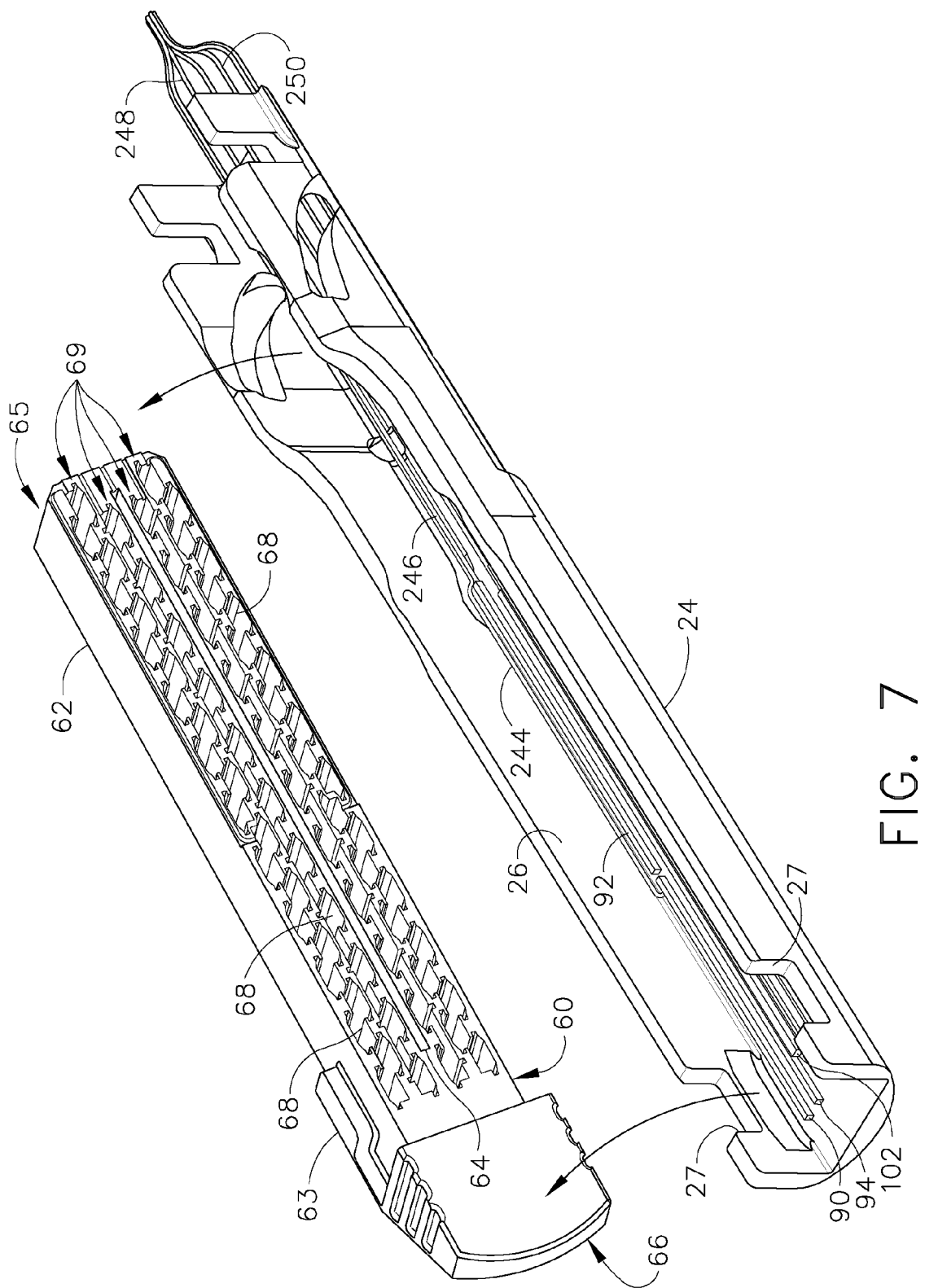
FIG. 7 is another exploded assembly view of the end effector and a staple cartridge.
Figure 8:
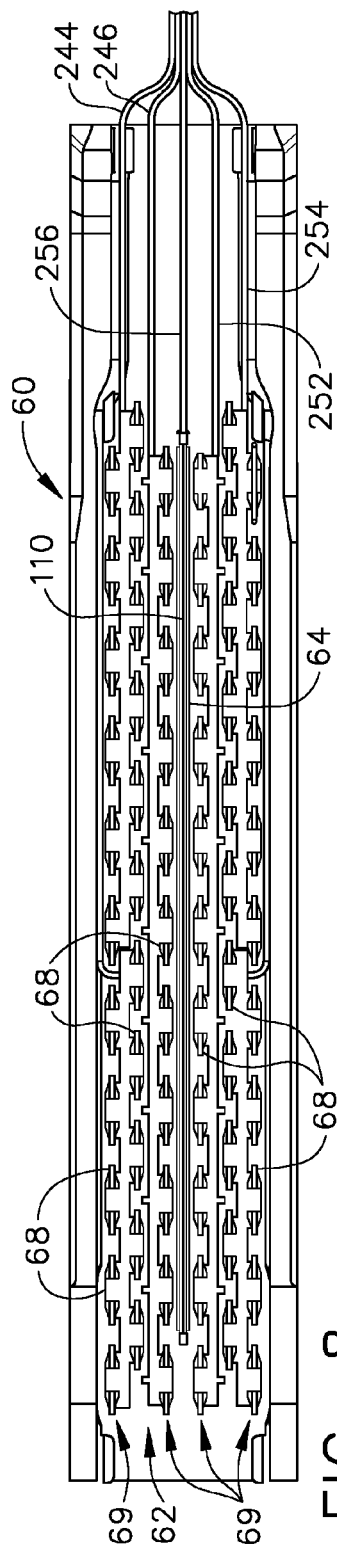
FIG. 8 is a plan view of a staple cartridge installed in an end effector depicted in FIGS. 6 and 7.
Figure 9:
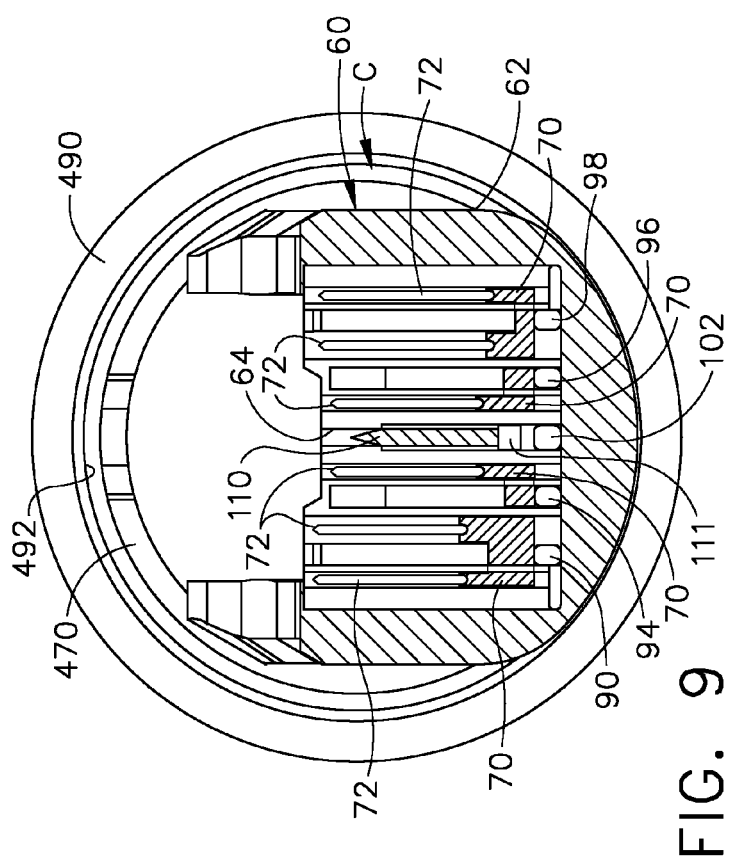
FIG. 9 is a cross-sectional end view illustrating the end effector inserted into a trocar passageway.
Figure 11:
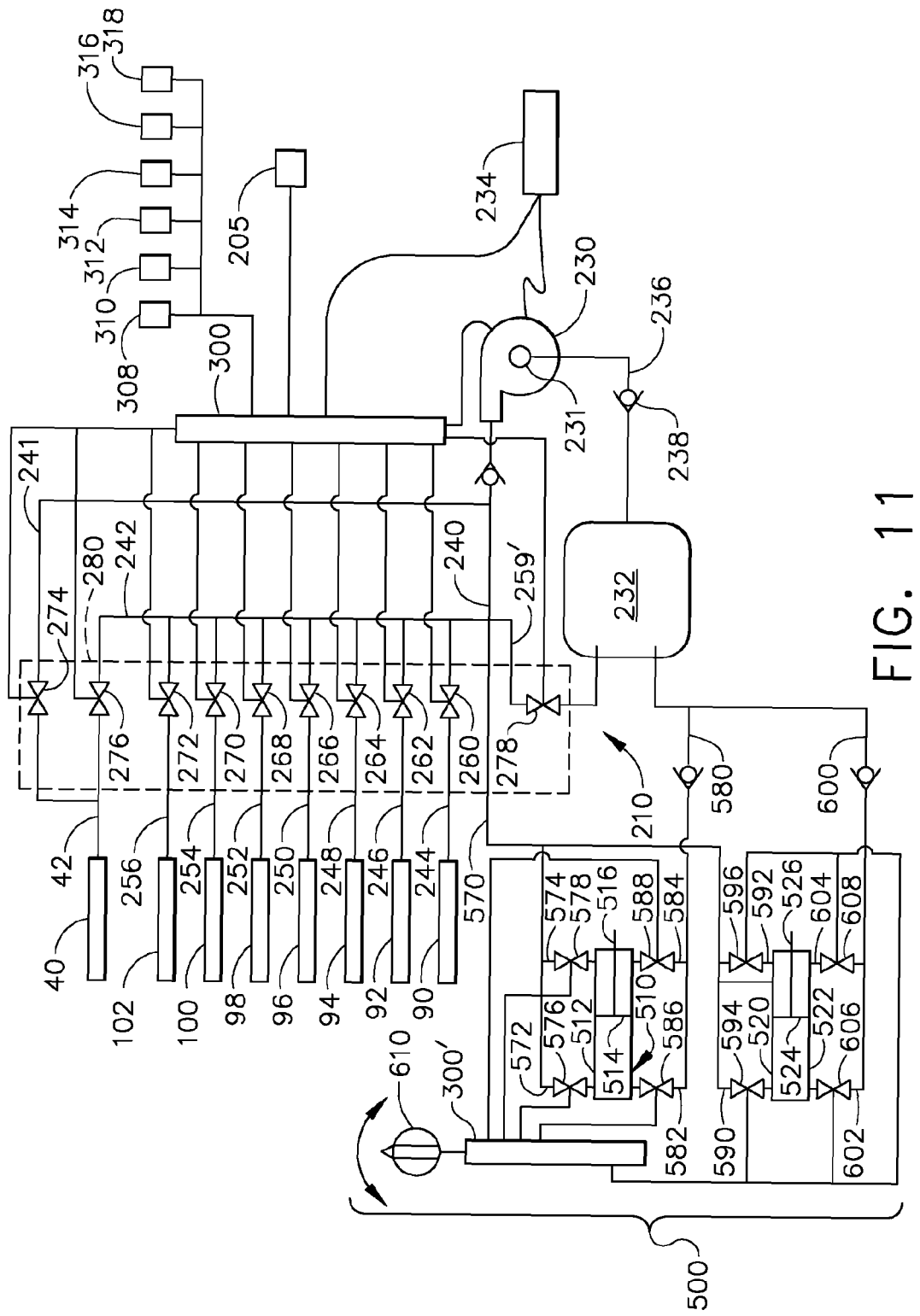
FIG. 11 is a schematic depiction of one hydraulic system embodiment of the present invention.
Figure 12:
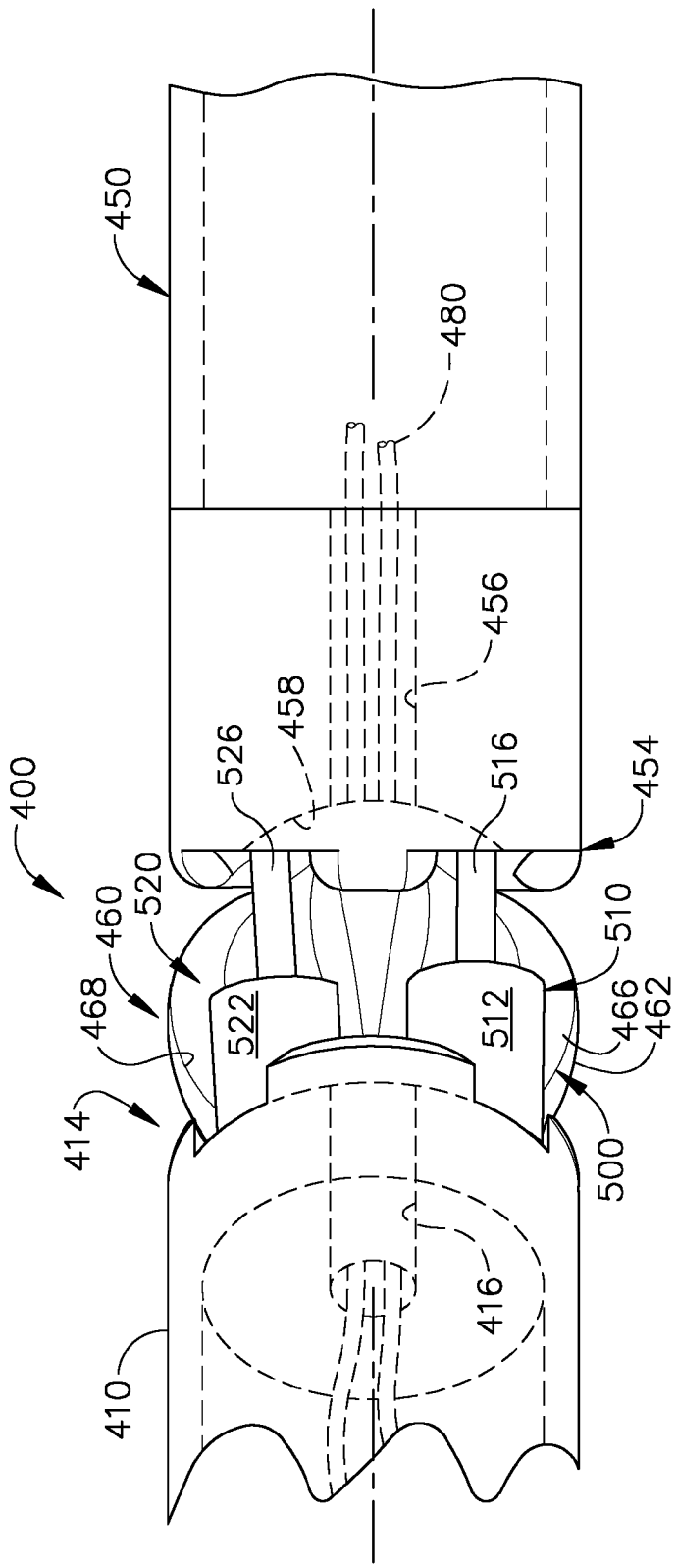
FIG. 12 is a partial perspective view of one non-limiting embodiment of an articulation joint of the present invention in an articulated position.
Figure 13:
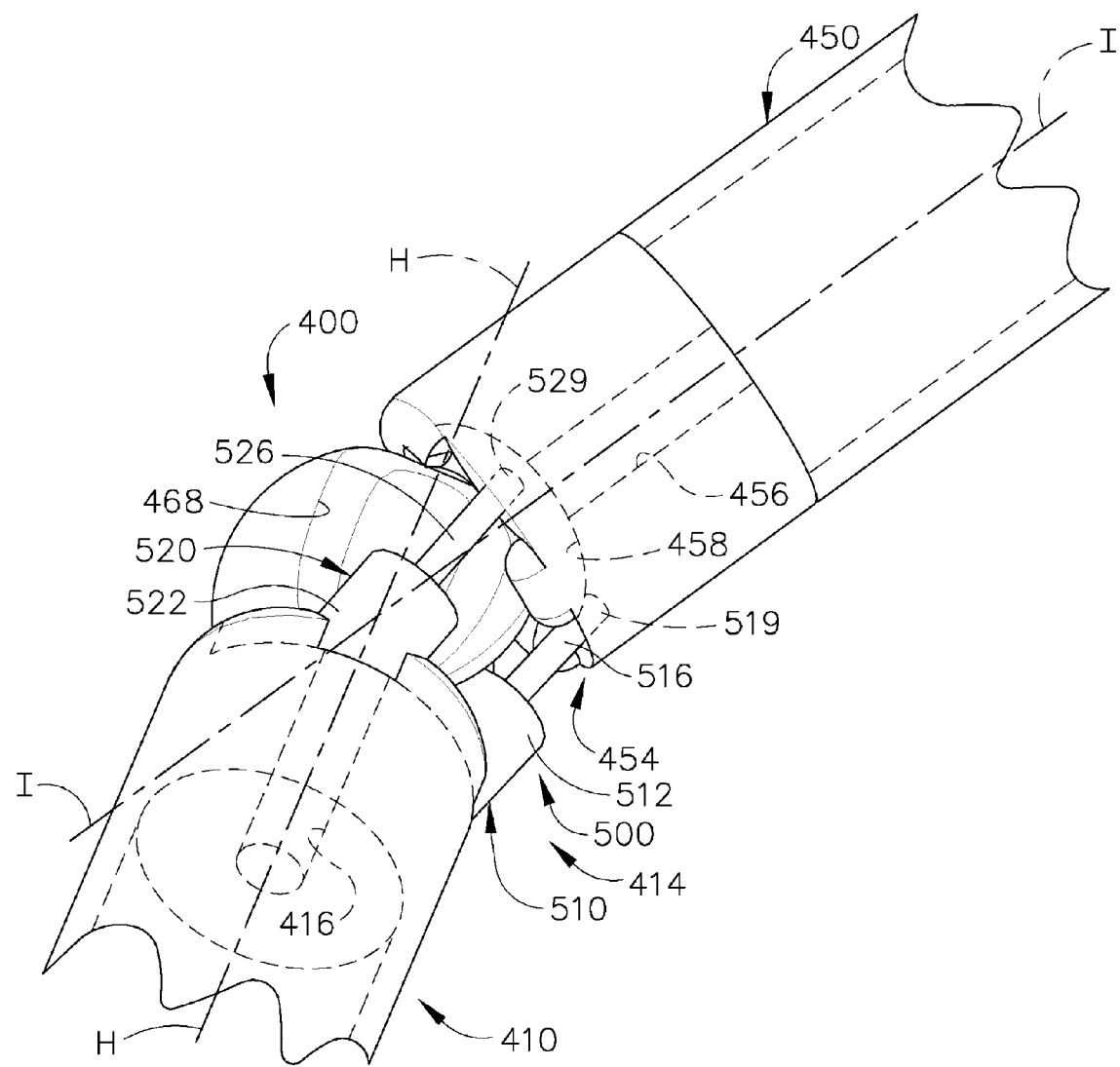
FIG. 13 is another partial perspective view of the articulation joint depicted in FIG. 12 in an articulated position.
Figure 14:
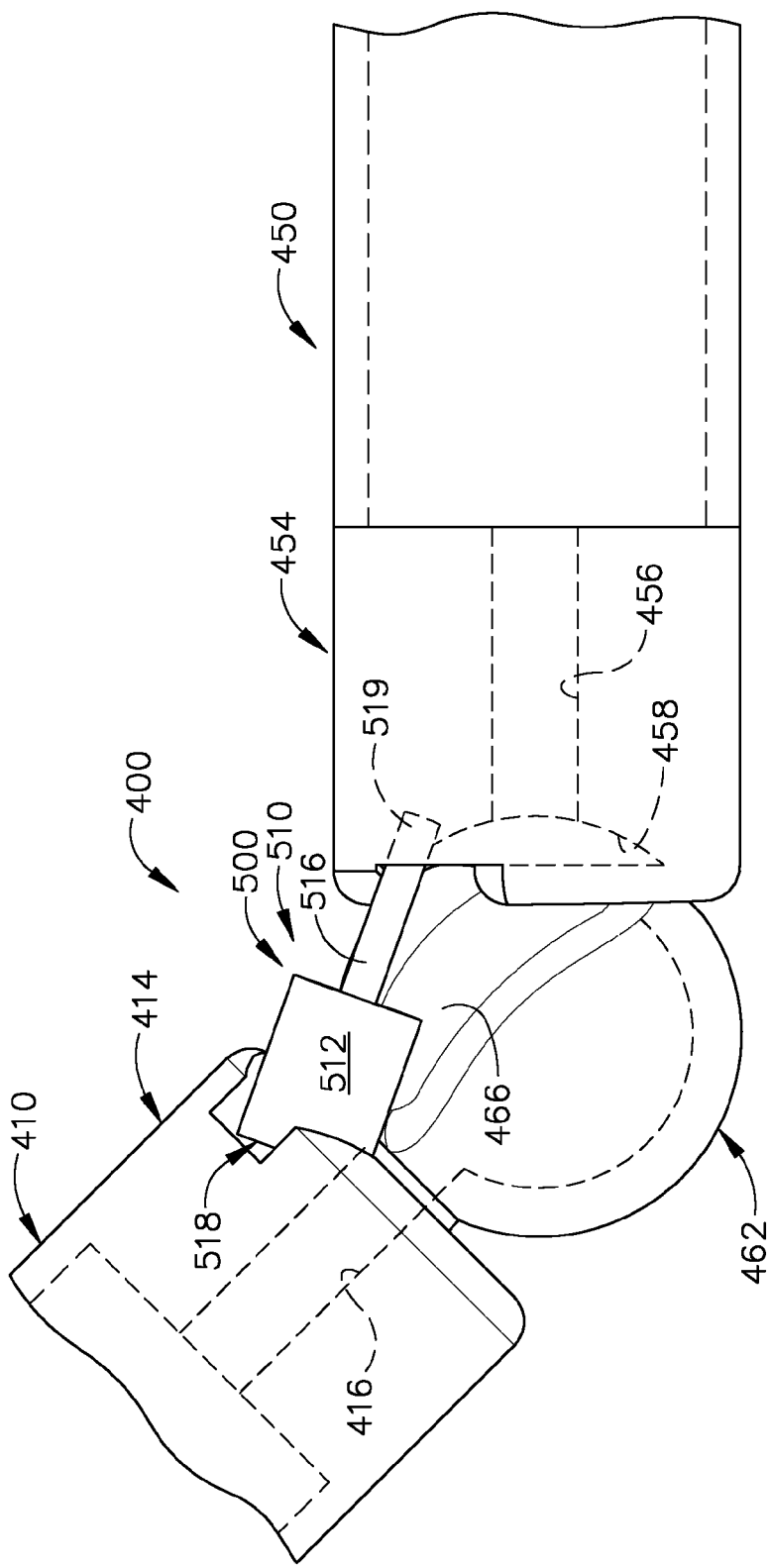
FIG. 14 is another partial perspective view of the articulation joint embodiment depicted in FIGS. 12 and 13 in an articulated position.

In one embodiment, the staple drivers 70 are driven in an "upward" (toward the anvil 28) direction by a series of hydraulically actuated bladders 90, 92, 94, 96, 98, 100 situated within the elongated slot 26 of the end effector 22 and arranged such that when the bladders 90, 92, 94, 96, 98, 100 are inflated, they drive or "fire" the corresponding drivers 70 and their respective staples 72 toward the anvil 28. As the ends of the staple legs contact the corresponding staple forming pockets 32 in the anvil 28, they are bent over to close the staple 72. Various firing arrangements are disclosed in the above-mentioned patent application entitled SURGICAL INSTRUMENT HAVING A HYDRAULICALLY ACTUATED END EFFECTOR" which has been herein incorporated by reference. Pressurized fluid or air is supplied to the bladders 90, 92, 94, 96, 98, 100 through a series of supply lines as shown in FIGS. 6 and 11.

Also in one embodiment, to facilitate cutting of tissue 8 clamped in the end effector 22, a hydraulically actuated cutting bar 110 is operatively mounted within the elongated channel 26 and arranged to be received within the elongated slot 64 in the cartridge body 62 when the cartridge 60 is mounted within the end effector 22. The cutting bar 110 extends longitudinally along the elongate slot 64 and is mechanically coupled to or otherwise supported on a support bar 111 which is attached to a hydraulic cutting bladder 102. By introducing a pressurized fluid or air into the cutting bladder 102, the cutting bar 110 is forced upward (represented by arrow A in FIG. 4) thereby causing the cutting bar 110 to sever the tissue 8 that is clamped between the anvil 28 and the cartridge 60. After the cutting bar 110 has severed the tissue 8, the pressurized fluid is permitted to exit the cutting bladder 102 to thereby permit the bladder 102 to deflate and permit the cutting bar 110 to move downward (arrow "B" in FIG. 3) to its retracted or unfired position. Pressurized fluid or air is supplied to the cutting bladder 102 by supply line 256.

As can be seen in FIGS. 1 and 2, the handle assembly 200 may house a hydraulic system generally designated as 210 for controlling the operation of the end effector 22. One embodiment of a hydraulic system 210 that may be employed to control the end effector 22 is depicted in schematic form in FIG. 11. In this non-limiting embodiment, a conventional hydraulic pump assembly 230 that includes a fluid reservoir 232 is employed to supply pressurized fluid to the various bladders. In one embodiment, the pump 230 is powered by a battery 234 supported within the handle assembly 200. However, the pump 230 could also be powered by other means, such as by alternating current or by a mechanical actuator. The pump 230 may be fluidically coupled to the reservoir 232 by supply line 236 that may have a conventional check valve 238 therein. See FIG. 11. As used herein, the term "fluidically coupled" means that the elements are coupled together with an appropriate supply, return, discharge, etc. line or other means to permit the passage of pressurized fluid medium, air, etc. therebetween. As used herein, the term "line" as used in "supply line", "discharge line" or "return line" refers to an appropriate fluid passage formed from conduit, pipe, tubing, etc. for transporting pressurized fluid, air, etc. from one component to another.

In one embodiment, a discharge line 240 attached to the discharge port 231 of the pump 230 is piped to a manifold 242 that has designated supply lines for each bladder coupled thereto. For example, in the embodiment depicted in FIG. 11, a supply line 244 is coupled to bladder 90 and has a control valve 260 therein for controlling the flow of pressurized fluid through the line 244 to bladder 90. Supply line 246 is coupled to bladder 92 and has a control valve 262 therein. Supply line 248 is coupled to bladder 94 and has a control valve 264 therein. Supply line 250 is coupled to bladder 96 and has a control valve 266 therein. Supply line 252 is coupled to bladder 98 and has a control valve 268 therein. Supply line 254 is coupled to bladder 100 and has a control valve 270 therein. Supply line 256 is coupled to cutting bladder 102 and has control valve 272 therein. Supply line 42 is coupled to the anvil bladder 40 and the supply line 240 by line 241. A supply valve 274 is provided in line 241 for controlling the flow of pressurized fluid thereto and a return valve 276 is provided to permit the fluid to return from the bladder 40 into the manifold line 242 and through a return line 259 that is attached to the manifold 242 and the reservoir 232. As can be seen in FIG.

11, the return line 259 may have a return valve 278 therein. Valves 262, 264, 266, 268, 270, 272, 274, 276, 278 comprise a valve unit, generally designated as 280. In various non-limiting embodiments, the valves 262, 264, 266, 268, 270, 272, 274, 276, 278 may each comprise electrically actuated valves, such as, for example, piezo valves or Electro Active Polymer (EAP) valves which may be configured in response to an electrical signal. However, other suitable valve and valve arrangements could be employed.

The above-described valves may be operated by a control circuit 300 in response to input received from input buttons, such as buttons 308, 310, 312, 314, and/or 316 located on handle. The control circuit may also be powered by the battery 234 and comprise a suitable circuit capable of generating signals for configuring valve unit 280 in response to input from buttons 308, 310, 312, 314, 316 and/or from other portions of the handle such as a closure trigger 206 and/or a firing trigger 208 that are pivotally coupled thereto. In one non-limiting embodiment, the control circuit 300 may include a microprocessor and other related components including Random Access Memory (RAM), Read Only Memory (ROM), etc. In other non-limiting embodiments, the control circuit 300 may include various logical circuit elements.

As can be seen in FIGS. 1 and 2, in one non-limiting embodiment, the handle assembly 200 of the instrument 10 includes a pistol grip 204 that includes a closure trigger 206 that is pivotally attached thereto to commence closure of the anvil 28. In one embodiment, a closure trigger sensor 205 is employed to sense when the closure trigger 206 has been pivoted to the closed position. The closure trigger sensor 205 communicates with the control circuit to open the return valve 276 and return valve 278 and close supply valve 274 to permit the pressurized fluid to return from the anvil bladder 28 into the reservoir 232. The anvil 28 is then pivoted to the closed position by the return spring 23. The closure trigger 206 may be retained in the closed position by a release button latch arrangement 36 of the type disclosed in U.S. Pat. No. 6,905,057 to Jeffrey S. Swayze and Frederick E. Shelton, IV, entitled SURGICAL STAPLING INSTRUMENT INCORPORATING A FIRING MECHANISM HAVING A LINKED RACK TRANSMISSION, the disclosure of which is herein incorporated by reference in its entirety. Another non-limiting embodiment links the closure trigger 206 to the tube assembly 452 and causes it to move distally driving the distal tube 410 over the end effector assembly 24 closing the system.

When the end effector 22 is in the closed position, it may be inserted through the trocar 490. See FIG. 9. To reopen the end effector 22, the release button 36 is pressed to unlatch the closure trigger 206 to enable it to pivot away from the firing trigger 208 to an open position. When in the open position, the closure trigger sensor 205 signals the control circuit 300 to power pump 230 and open supply valve 274 and close return valve 276. Pressurized fluid is then pumped into the anvil bladder 40 to pivot the anvil 28 to the open position. When the clinician has oriented the end effector 22 such that the desired tissue is located between the open anvil 28 and the cartridge 60, the closure trigger 206 is pivoted to the closed position and latched. Valves 276 and 278 are opened and valve 241 is closed. Valves 276 and 278 are opened for a sufficient time to permit the fluid in the anvil bladder 40 to be returned therefrom through the lines 42, 242 and 259. Thereafter, those valves are closed. As indicated above, the use of the hydraulically powered bladder and return spring arrangement described herein is just one type of structure that may be employed to open and close the anvil 28. Other anvil control arrangements may be employed without departing from the spirit and scope of the present invention and, therefore, the protection afforded to the various embodiments of the present invention should not be limited solely to such bladder and return spring arrangement.

Input buttons 308, 310, 312, 314, 316 may provide input signals to the control circuit 300 in any suitable way. In one non-limiting embodiment, each input button 308, 310, 312, 314, 316 may correspond to a particular valve or valves for controlling the inflation of one or more bladders. While five actuation buttons are shown for this non-limiting embodiment, the reader will appreciate that other numbers of buttons may be employed. For example, if it is desirable to only actuate one stapling bladder at a time, a separate actuation button for each bladder may be provided. For example, button 308 may control valve 272 in the cutter supply line 256. By actuating that valve 272, pressurized fluid supplied by the pump 230 into the manifold 242 is permitted to flow through the supply line 256 into the cutting bladder 102. Likewise, if actuator button 310 is used to control valves 260, 262, activating the button 310 will cause the stapling bladders 90 and 92 to inflate and fire their corresponding staples 72. Multiple buttons may be selected to create firing patterns including more than one implement. In other non-limiting embodiments, each input button 308, 310, 312, 314, 316 may represent a pre-determined firing order and/or pattern. For example, selecting a button 308, 310, 312, 314, 316 may cause the control circuit 318 to configure the valve unit 304 such that hydraulic devices corresponding to particular surgical implements are fired when the firing trigger 28 is depressed. It will be appreciated that various embodiments may have more or fewer input buttons than are shown. In one embodiment, a firing trigger 208 is pivotally attached to the handle 200 outboard of the closure trigger 206 and one or more firing sensors (not shown) may be positioned to detect the position of the firing trigger. The firing sensors would then communicate with the control circuit 300 to control the various valves to permit pressurized fluid to flow to the various staple bladders to achieve a desired firing sequence.

In various non-limiting embodiments, the valve unit 280 may be configured to introduce a delay to the driving of one or more surgical implements included in the end effector 12. For example, it may be desirable to drive a cutting implement and then delay for a predetermined time before driving one or more zones of a stapling implement. The delay may be accomplished according to any suitable method. In one non-limiting embodiment, the control circuit 300 may configure the valve unit 280 to open a path for hydraulic fluid between the hydraulic pump 230 and a first surgical implement included in the end effector 12. When the firing trigger 28 is actuated, the pump 302 may generate pressurized hydraulic fluid, which drives the first surgical implement. The control circuit 300 may sense when the first surgical implement is driven (e.g., by sensing the position of the firing trigger 208) and begin a timer that counts off a predetermined delay time. At the expiration of the predetermined delay time, the control circuit 318 may configure the valve unit 280 to provide the pressurized hydraulic fluid to a second surgical implement. Hydraulic pressure generated at the actuation of the firing trigger 208 may be sufficient to drive the second surgical implement, or in various embodiments, the hydraulic pump 230 may be utilized to generate additional hydraulic pressure.

In one non-limiting embodiment of the present invention, the end effector 22 may be attached to the handle assembly 200 by an articulating joint assembly, generally designated as 400. As can be seen in FIGS. 1, 2, and 12-14, the articulating joint assembly 400 includes a distal tube segment 410 that has a distal end 412, a proximal end 414, and a distal axis H-H.

The distal end 412 is mechanically (e.g., rigidly or slidably connected—depending upon the anvil closure arrangement employed) coupled to the end effector body 24. The distal tube 410 segment may be partially hollow with the proximal end being solid with a hose/wire receiving passage 416 therethrough.

The joint assembly 400 further includes a proximal tube segment 450, that has a proximal end 452, a distal end 454, and a proximal axis I-I. The proximal end 452 is attached to the handle assembly 200. In one embodiment, for example, the proximal end 452 may be attached to the handle assembly 200 by an internal channel retainer that is grounded to the handle assembly. However, other fastening arrangements could be employed. In one embodiment, the distal end 454 is solid and has a hollow hose/wire-receiving passage 456 therethrough. The remaining portion of the tube segment 450 may be hollow to permit passage of hoses and/or wires therethrough.

In one embodiment, the distal tube segment 410 is pivotally coupled to the proximal tube segment 450 by a ball joint assembly 460. In one embodiment, the ball joint assembly 460 comprises a hollow ball member 462 that is mounted to or formed on the proximal end 414 of the distal tube segment 410. The ball member 462 is substantially hollow or has a hollow passageway therein to permit the passage of hoses and/or wires therethrough. The ball member 462 is received in a socket 458 provided in the distal end of the proximal tube segment 450, such that the ball member 462 is free to pivot therein.

In one embodiment, an actuation assembly, generally designated as 500 is employed to articulate the distal tube segment 410 relative to the proximal tube segment 450. As can be seen in FIGS. 11-14, in one non-limiting embodiment, two articulation cylinders 510, 520 are employed. First articulation cylinder 510 may comprise a conventional hydraulic or pneumatic cylinder that has a first housing 512 that contains a first piston 514 therein. A first piston rod or first actuation rod 516 is attached to the first piston 514 and protrudes out of the first housing 512. Movement of the piston 514 within the first housing 512 in response to the admission of pressurized fluid or air on one side or the other side of the piston 514 causes the first actuation rod 516 to be extended out of the first cylinder housing 512 or into the first cylinder housing 512. A distal end 518 of the first housing 512 is pivotally (pinned) or otherwise rigidly attached to the proximal end 414 of the distal tube segment 410. The first actuation rod 516 is fabricated from a flexible material such as rubber or the like and the free end 519 thereof is rigidly affixed to the distal end 454 of the proximal tube segment 450. The free end 519 of the first actuation rod 516 may be attached to the distal end 454 by gluing, threads, etc. A first indentation 466 or a series of indentations are provided in the outer surface 464 of the ball member to provide the requisite clearance for the first actuation rod 516 and also the end of the first cylinder housing 512.

Also in this non-limiting embodiment, the second articulation cylinder 520 may comprise a conventional hydraulic or pneumatic cylinder that has a second housing 522 that contains a second piston 524 therein. A second piston rod or second actuation rod 526 is attached to the second piston 526 and protrudes out of the second housing 522. Movement of the second piston 524 within the second cylinder housing 522 in response to the admission of pressurized fluid or air on one side or the other side of the second piston 524 causes the actuation rod 526 to be extended out of the second cylinder housing 522 or into the second cylinder housing 522. The second cylinder housing 522 is pivotally (pinned) or otherwise rigidly attached to the proximal end 414 of the distal tube segment 410. The second actuation rod 526 is fabricated from a flexible material such as rubber or the like and the free end 529 thereof is rigidly affixed to the distal end 454 of the proximal tube segment 450. The free end 529 of the second actuation rod 526 may be attached to the distal end 454 by gluing, threads, etc. A second indentation 468 or a series of indentations are provided in the outer surface 464 of the ball member 462 to provide the requisite clearance for the second actuation rod 526 and also the end of the second cylinder housing 522.

The first and second articulation cylinders 510, 520 may be powered by the hydraulic system 210 or they may be powered by a separate hydraulic system. FIG. 11 depicts one method of controlling the first and second articulation cylinders 510, 520. As can be seen in that Figure, a supply line 570 is connected to the supply line 240 from the pump 230. A first portion 572 of the supply line 570 is attached to a first supply port in the first cylinder housing 512 for supplying pressurized fluid or air into the first cylinder housing 512 on one side of the first piston 514 and a second portion 574 of the supply line 570 is attached to a second supply port in the first housing 512 for supplying pressurized fluid or air into the first housing 512 on the other side of the first piston 514. A first supply valve 576 is mounted in the first portion 572 of the supply line 570 and a second supply valve 578 is mounted in the second portion 574 of the first supply line 570. An exhaust or return line 580 is provided to return the pressurized fluid from the first housing 512 to the fluid reservoir 232. The return line 580 has a first portion 582 and a second portion 584 attached to ports in the first housing 512. A first return valve 586 is mounted in the first portion 582 of the return line 580 and a second return valve 588 is mounted in the second portion 584 of the return line.

The supply line 570 further has a third portion 590 that is coupled to a third supply port in the second housing 522 on one side of the second piston 524 and the supply line 570 has a fourth portion 592 coupled to a fourth supply port in the second housing 522 on the other side of the second piston 524. A valve 596 is mounted in the third portion 590 and another valve 598 is mounted in fourth portion 592 of the supply line 570. Another return line 600 is provided to permit the pressurized fluid, air, etc. to return to the reservoir 232 from the housing 522 during actuation of the cylinder 520. The return line 600 has a third portion 602 attached to a third return port in the second housing 522 on one side of the second piston 524 and a fourth portion 604 of the return line 600 is coupled to a fourth return port in the second housing 522 on the other side of the second piston 524. A return valve 606 is provided in the third portion 602 of the return line 600 and another return valve 608 is provided in the portion 604 of the return line 600.

The valves may be controlled by the control circuit 300 or a second control circuit 300' of the type described above that may include a microprocessor and other related components including Random Access Memory (RAM), Read Only Memory (ROM), etc. In other non-limiting embodiments, the control circuit 300' may include various logical circuit elements. A conventional multiposition switch 610 or a series of switches, push buttons etc. may be connected to the second control circuit 300' for controlling the valves 576, 578, 586, 588, 594, 596, 606, 608 to control the cylinders 510, 520 in the manners necessary to achieve the desired degree and direction of articulation.

When pivotally attached together as described above, the proximal and distal tube segments 410, 450 form a tube assembly 470 that has a passageway 472 or passageways for supporting the supply lines (collectively designated as 480)

between the end effector 22 and the handle 200. It will be appreciated that the tube assembly 470 has a circumference "C" and shape such that when the distal tube 410 segment is coaxially aligned with the proximal tube segment 450, the tube assembly 470 may be inserted through the passageway 492 in a trocar 490. See FIG. 9. In one embodiment, the first and second tube segments 410, 450 have a round cross-sectional shape and are sized to be axially inserted through a round trocar passageway 492. The outer diameters of each the distal tube segments 410, 450 are less than the inner diameter of the trocar passageway 492 to facilitate axial insertion of the tube assembly 470 through the trocar passage 492 and, if desired or necessary, rotation of the tube assembly 470 within the trocar passageway 492. For example, if the trocar passageway 492 has an inner diameter of approximately 12.8 mm (0.503 inches), the maximum outer diameter of tube assembly 470 (and of each of the tube segments 410, 450) may be approximately 12.7 mm (0.500 inches). It is conceivable that, for applications wherein the ability to rotate the tube assembly 470 within the trocar passageway 492 is not necessary or desirable, trocars with passageways having non-circular cross-sections could be employed. In those cases, the tube assembly would have a cross-sectional shape that would facilitate axial insertion of the tube assembly through the trocar passageway and may closely resemble the cross-sectional shape of the trocar passageway. Thus, the various embodiments of the subject invention should not be limited to devices having a tube assembly with a round cross-sectional shape.

FIG. 1 illustrates the joint assembly in a non-articulated position that would enable the tube assembly 470 to be inserted into the trocar. After the surgical implement 12 has be inserted through the trocar 490 and it becomes desirable to articulate the implement 12, the clinician activates the control circuit 300' through switch 610. Depending upon the degree and direction of articulation desired, the first piston 516 and the second piston 526 may either both be extended, one extended and one retracted or both retracted to cause the ball member 462 to pivot in the socket to achieve the desired amount of articulation. The pistons 516 and 526 are extended by the clinician by activating multiposition switch or buttons located on the handle assembly to cause the control circuit 300' to open and close the various control valves 576, 578, 586, 588, 594, 596, 606, 608. The reader will appreciate that the first and second actuation rods 516, 526 may, depending upon the forces, tend to bend rather than pivot during actuation and it is the deflection and buckling of these rods 516, 526 that further causes the distal tube segment 410 to articulate relative to the proximal tube segment 450. Moreover, if the articulation cylinders 510,520 are not aligned 180 degrees about the longitudinal axis of the device, they can be used to articulate the end effector in multiple planes as well as merely pivoting it about a point perpendicular to the longitudinal axis. Such pivotal flexibility is made possible through use of the ball joint arrangement of this embodiment. Such arrangement represents a significant improvement over other arrangements that can only articulate about a single axis.

The hydraulic control system described above for actuating the articulation cylinders 510, 520 is but one example of a control system that may be used. The reader will appreciate that a variety of different control arrangements may be employed to activate the articulation cylinders without departing from the spirit and scope of the present invention. For example, the articulation cylinders 510, 520 as described above require the admission of pressurized fluid/air to move their respective pistons in both directions. Other cylinders that employ springs or other mechanisms for returning the pistons to a starting position may be employed along with appropriate valve and hydraulic fluid supply arrangement that are within the capabilities of the skilled artisan may be employed. It will be further appreciated that, while two articulation cylinders have been described above, other embodiments of the present invention may employ only one articulation cylinder or more than two articulation cylinders. Also, while the ball member 462 has been described as being non-movably mounted to the distal tube segment 410 with the socket 458 provided in the proximal tube segment 450, those of ordinary skill in the art will understand that the ball member 462 may be non-movably attached to the proximal tube segment 450 and the socket 458 provided in the distal tube segment 410 in other non-limiting embodiments without departing form the spirit and scope of the present invention.

Figure 15:
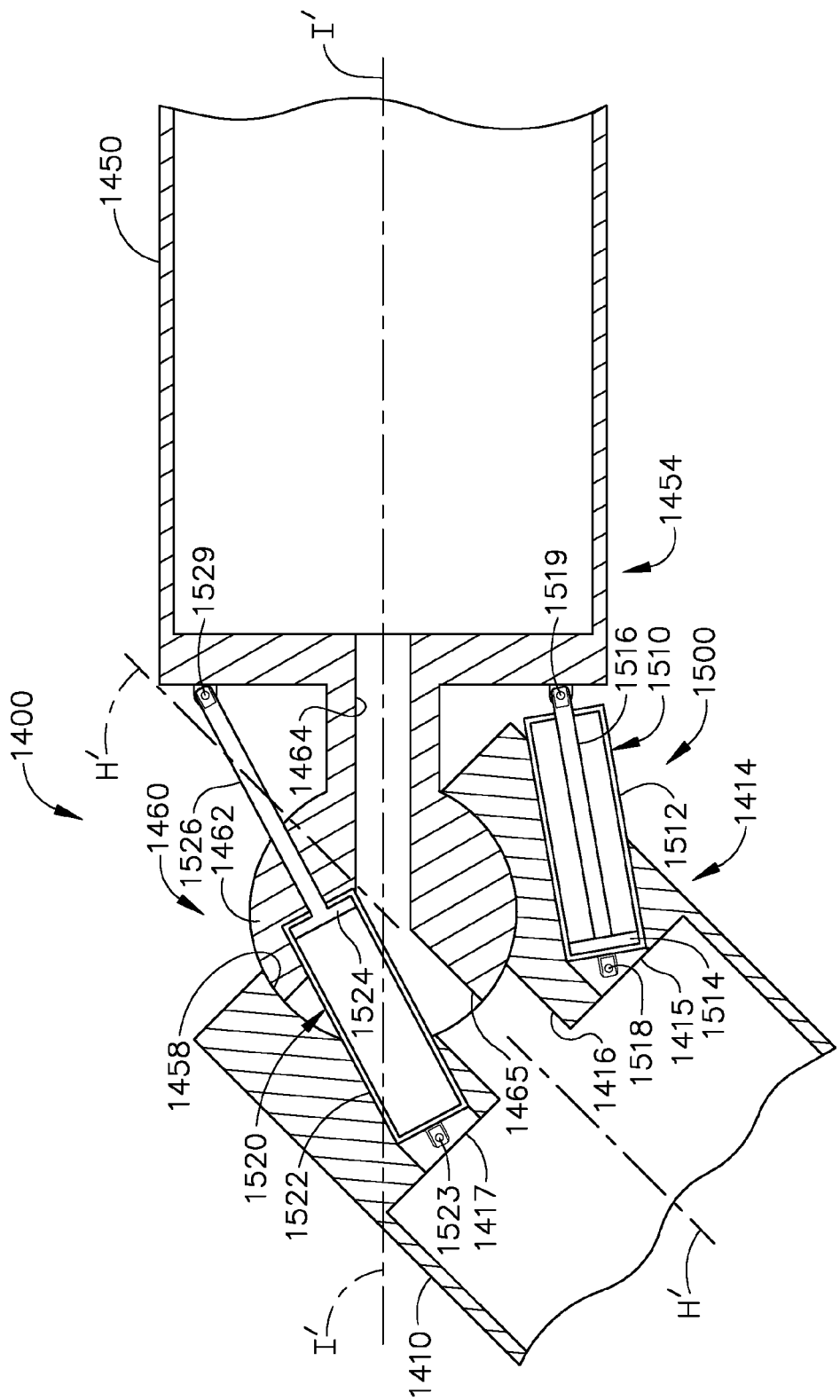
FIG. 15 is a partial cross-sectional view of another non-limiting embodiment of an articulation joint of the present invention in an articulated position.

FIG. 15 illustrates another articulation joint assembly 1400 embodiment of the present invention. As can be seen in that Figure, distal tube segment 1410 has a proximal end 1414 and a distal axis H'-H'. Although not shown in FIG. 15, the distal tube segment 1410 has a distal end 1412 that is mechanically coupled to the end effector body 24. Depending upon the anvil closure arrangement employed, the distal end 1412 may be non-movably attached to the end effector body or by a cable, flexible member or pivotable member. The distal tube 1410 segment may be partially hollow with the proximal 1414 end being solid with a hose/wire receiving passage 1416 therethrough.

The joint assembly 1400 further includes a proximal tube segment 1450, that has a distal end 1454, and a proximal axis I'-I'. Although not shown in FIG. 15, the proximal tube segment 1450 has a proximal end that is mechanically attached to the handle assembly 200.

In one embodiment, the distal tube segment 1410 is pivotally coupled to the proximal tube segment 1450 by a ball joint assembly 1460. In one embodiment, the ball joint assembly comprises a hollow ball member 1462 that is mounted to or is formed on the distal end 1454 of the proximal tube segment 1450. The ball member 1462 has a hollow passageway 1464 that has a flared or otherwise enlarged end portion 1465 to enable it to communicate with the passageway 1416 such that, regardless of the position of the ball member 1462, the hoses 480 and/or wires extending therethrough will not be pinched or otherwise damaged. The ball member 1462 is received in a socket 1458 provided in the proximal end 1414 of the distal tube segment 1410, such that the ball member 1462 is free to pivot or rotate therein.

In one embodiment, an actuation assembly, generally designated as 1500 is employed to articulate the distal tube segment 1410 relative to the proximal tube segment 1450. As can be seen in FIG. 15, in one non-limiting embodiment, two articulation cylinders 1510, 1520 are employed. First articulation cylinder 1510 may comprise a conventional hydraulic or pneumatic cylinder that has a first housing 1512 that contains a first piston 1514 therein. A first piston rod or first actuation rod 1516 is attached to the first piston 1514 and protrudes out of the first housing 1512. Movement of the piston 1514 within the first housing 1512 in response to the admission of pressurized fluid or air on one side or the other side of the piston 1514 causes the first actuation rod 1516 to be extended out of the first cylinder housing 1512 or into the first cylinder housing 1512. A distal end 1518 of the first housing 1512 is pivotally (pinned) to a portion 1415 of the proximal end 1414 of the distal tube segment 1410. The outer surface of the proximal end 1414 in the area of the first cylinder housing 1512 may be contoured to facilitate pivotal movement of the cylinder housing 1512. The first actuation rod 1516 may be fabricated from a flexible material such as rubber or the like or it may be fabricated from rigid material. The free end 1519 of the actuation rod 516 is pivotally pinned to or otherwise attached to the distal end 1454 of the proximal tube segment 1450.

Also in this non-limiting embodiment, the second articulation cylinder 1520 may comprise a conventional hydraulic or pneumatic cylinder that has a second housing 1522 that contains a second piston 1524 therein. A second piston rod or second actuation rod 1526 is attached to the second piston 1524 and protrudes out of the second housing 1522. Movement of the second piston 1524 within the second cylinder housing 1522 in response to the admission of pressurized fluid or air on one side or the other side of the second piston 1524 causes the actuation rod 1526 to be extended out of the second cylinder housing 1522 or into the second cylinder housing 1522. The distal end 1523 of the second cylinder housing 1522 is pivotally (pinned) to a portion 1417 of the proximal end 1414 of the distal tube segment 1410. The outer surface of the proximal end 1414 in the area of the second cylinder housing 1522 may be contoured to facilitate pivotal movement of the cylinder housing 1522. The second actuation rod 1526 may be fabricated from a flexible material such as rubber or the like or it may be fabricated from rigid material. The free end 1529 of the actuation rod 1526 is pivotally pinned to or otherwise attached to the distal end 1454 of the proximal tube segment 1450.

The first and second articulation cylinders 1510, 1520 may be powered by the hydraulic system 210 in the same manner as was discussed in detail above with respect to cylinders 510, 520 or they may be powered by a separate hydraulic system. FIG. 11 depicts one method of controlling the first and second articulation cylinders 1510, 1520. The distal tube segment 1410 (and the end effector 22 attached thereto) may be articulated relative to the proximal tube 1450 in the direction shown in FIG. 15 by extending the actuation rod 1526 and retracting the actuation rod 1516. Likewise, the distal tube segment 1410 may be pivoted to a direction opposite to the direction shown in FIG. 15 by extending the actuation rod 1516 and retracting the actuation rod 1526. The control circuit 300' may actuate the cylinders 1510, 1520 in these manners in response to the position of the multiposition control switch 610 on the handle assembly 200. The reader will also appreciate that, while two articulation cylinders have been described above, other embodiments of the present invention may employ only one articulation cylinder if only one degree articulation is needed or desired. Also, while the ball member 1462 has been described as being non-movably mounted to the proximal tube 1450 with the socket 1458 provided in the distal tube segment 1410, those of ordinary skill in the art will understand that the ball member 1462 may be non-movably attached to the distal tube segment 1410 and the socket 1458 provided in the proximal tube segment 1450 in other non-limiting embodiments without departing from the spirit and scope of the present invention.

Figure 15A:
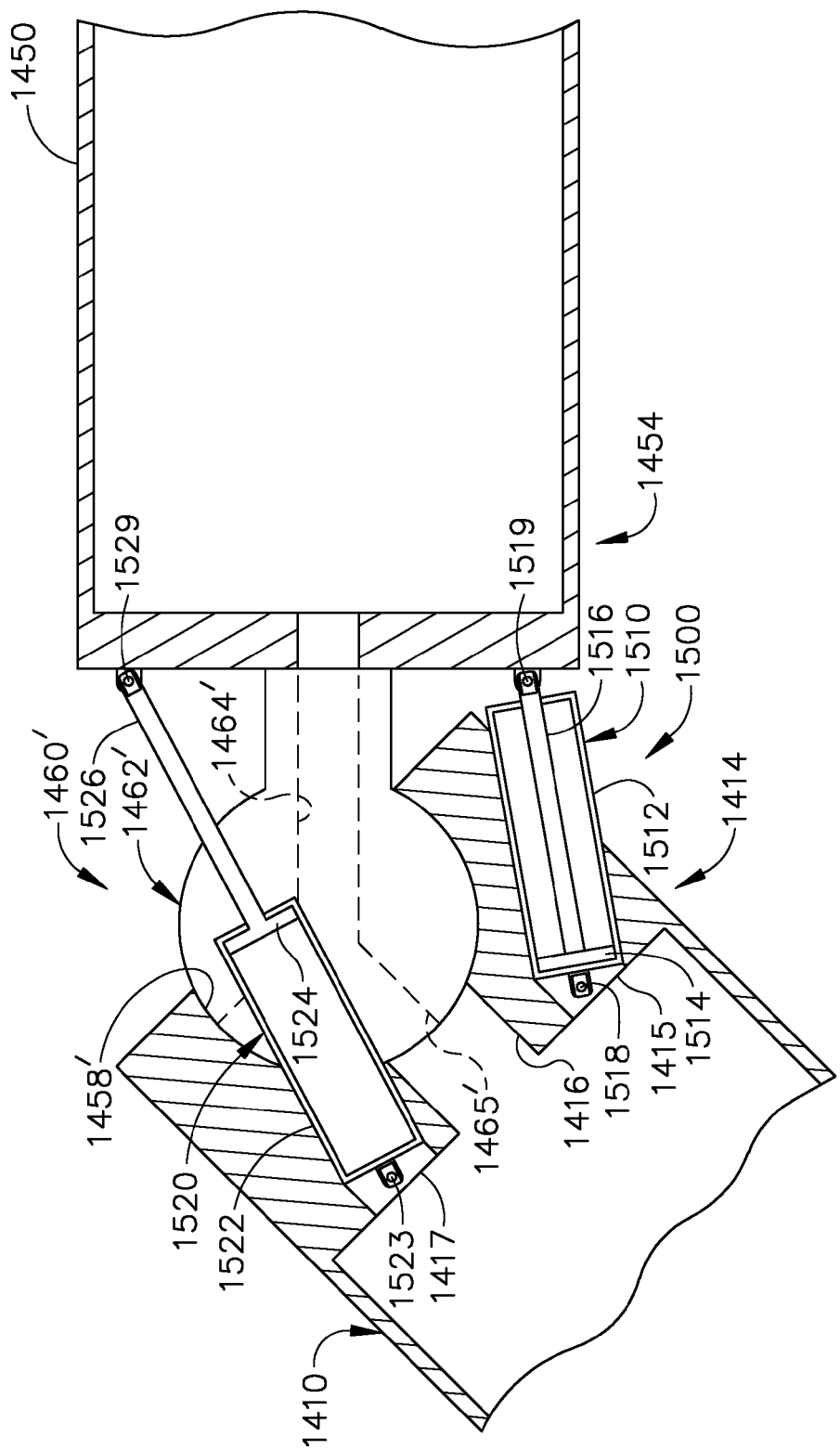
FIG. 15A is a partial cross-sectional view of another articulation joint of the present invention in an articulated position.

In an alternative embodiment depicted in FIG. 15A, the joint assembly 1460' comprises a round disc-like member 1462' instead of a ball shaped member. The disc 1462' has a hollow passageway 1464' that has a flared or otherwise enlarged end portion 1465' to enable it to communicate with the passageway 1416 such that, regardless of the position of the disc-like member 1462', the hoses 480 and/or wires extending therethrough will not be pinched or otherwise damaged. The disc-like member 1462' is received in a socket 1458' provided in the proximal end 1414 of the distal tube segment 1410, such that the disc-like member 1462' is free to pivot therein. If desired, the outer edge of the disc-like member 1462' could be provided with a tongue (not shown) that is received in a groove (not shown) in the socket wall to further stabilize the disc-like member 1462'. This embodiment otherwise employs actuators 1510 and 1520 as described above. Again, however, the reader will appreciate that, while two articulation cylinders have been described above, other embodiments of the present invention may employ only one articulation cylinder if only one degree articulation is needed or desired. Also, while the disc-like member 1462' has been described as being non-movably mounted to the proximal tube segment 1450 with the socket 1458' provided in the distal tube segment 1410, those of ordinary skill in the art will understand that the disc-like member 1462' may be non-movably attached to the distal tube segment 1410 and the socket 1458' provided in the proximal tube segment 1450 in other non-limiting embodiments without departing from the spirit and scope of the present invention.

Figure 16:
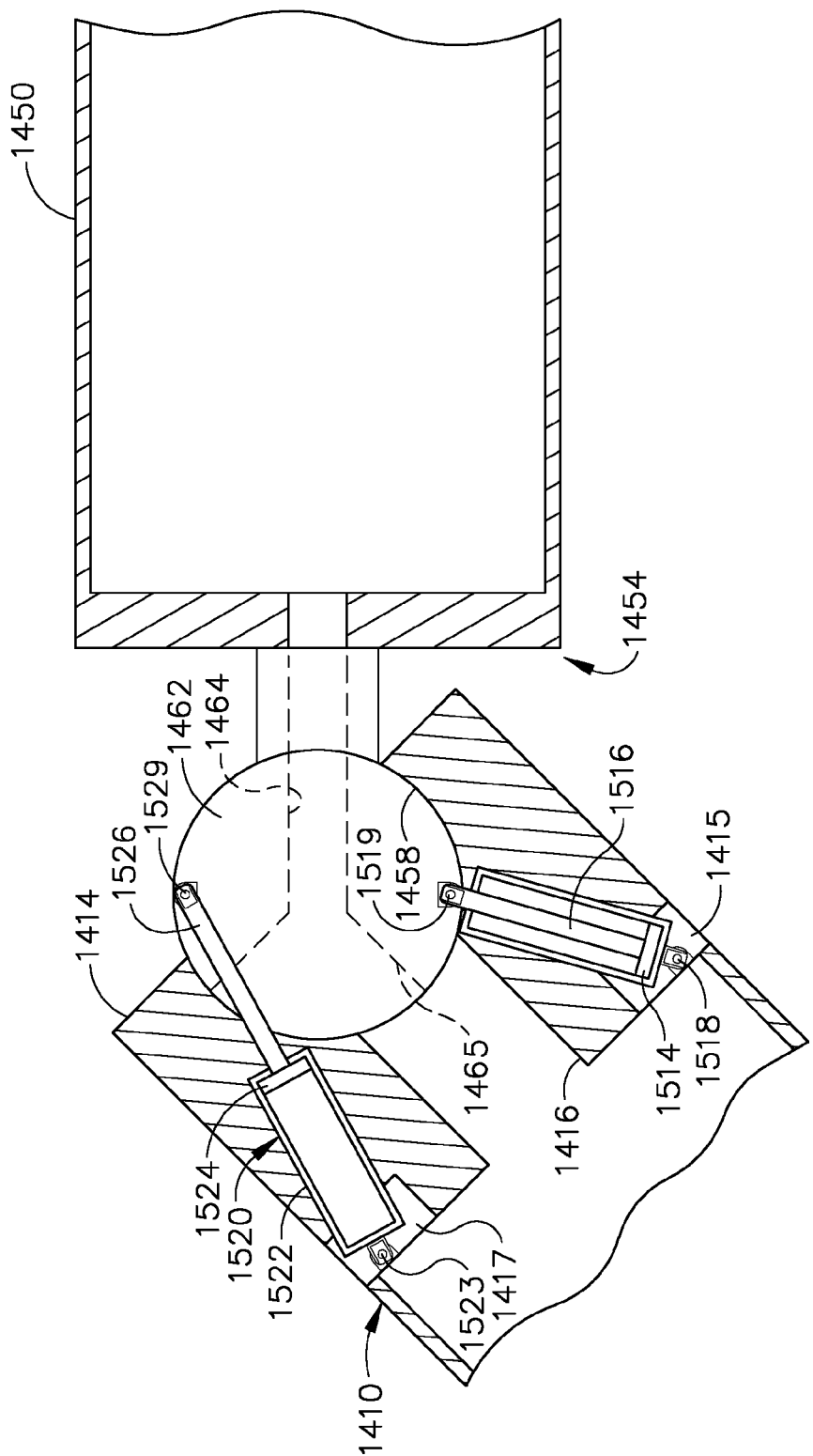
FIG. 16 is a partial cross-sectional view of another articulation joint of the present invention in an articulated position.

Another alternative embodiment is depicted in FIG. 16. As can be seen in this embodiment, the end 1519 of the first actuation rod 1516 of cylinder 1510 is attached to portion of the outer surface of the ball member 1462 and the end 1529 of the second actuation rod 1516 is also attached to a portion of the ball member 1462. This embodiment is otherwise identical in composition and operation as the embodiment depicted in FIG. 15 and described above. Again, however, the reader will appreciate that, while two articulation cylinders have been described above, other embodiments of the present invention may employ only one articulation cylinder if only one degree articulation is needed or desired. Also, while the ball member 1462 has been described as being non-movably mounted to the proximal tube segment 1450 with the socket 1458 provided in the distal tube segment 1410, those of ordinary skill in the art will understand that the ball member 1462 may be non-movably attached to the distal tube segment 1410 and the socket 1458 provided in the proximal tube segment 1450 in other non-limiting embodiments without departing from the spirit and scope of the present invention.

Figure 16A:
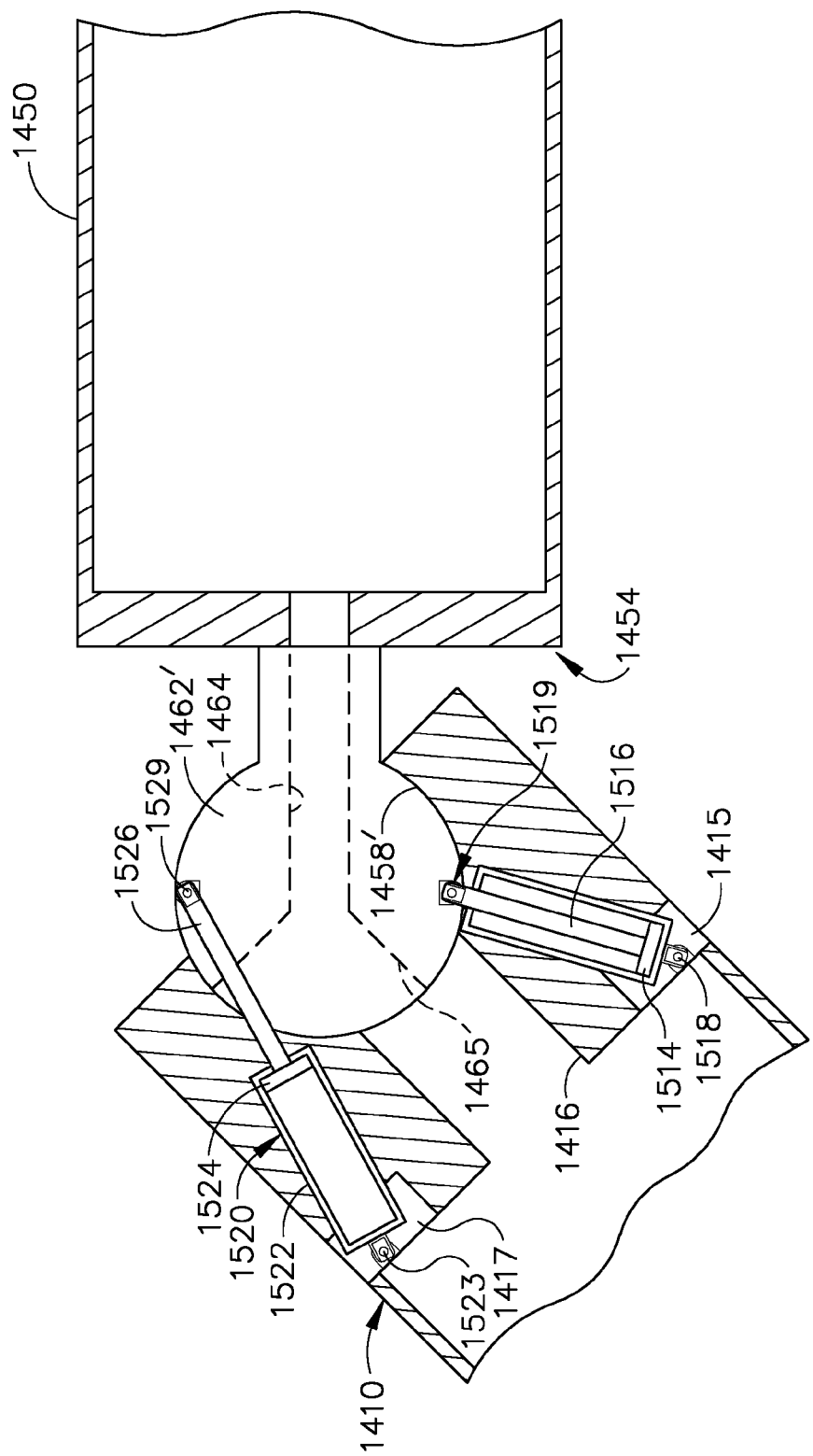
FIG. 16A is a partial cross-sectional view of another articulation joint of the present invention in an articulated position.

Another alternative embodiment is depicted in FIG. 16A. As can be seen in this embodiment, the end 1519 of the first actuation rod 1516 of cylinder 1510 is attached to portion of the outer surface of the disc-like member 1462' and the end 1529 of the second actuation rod 1516 is also attached to a portion of the disc-like member 1462'. This embodiment is otherwise identical in composition and operation as the embodiment depicted in FIG. 16A and described above. Again, however, the reader will appreciate that, while two articulation cylinders have been described above, other embodiments of the present invention may employ only one articulation cylinder if only one degree articulation is needed or desired. Also, while the disc-like member 1462' has been described as being non-movably mounted to the proximal tube segment 1450 with the socket 1458' provided in the distal tube segment 1410, those of ordinary skill in the art will understand that the disc-like member 1462' may be non-movably attached to the distal tube segment 1410 and the socket 1458' provided in the proximal tube segment 1450 in other non-limiting embodiments without departing from the spirit and scope of the present invention.

Figure 17:
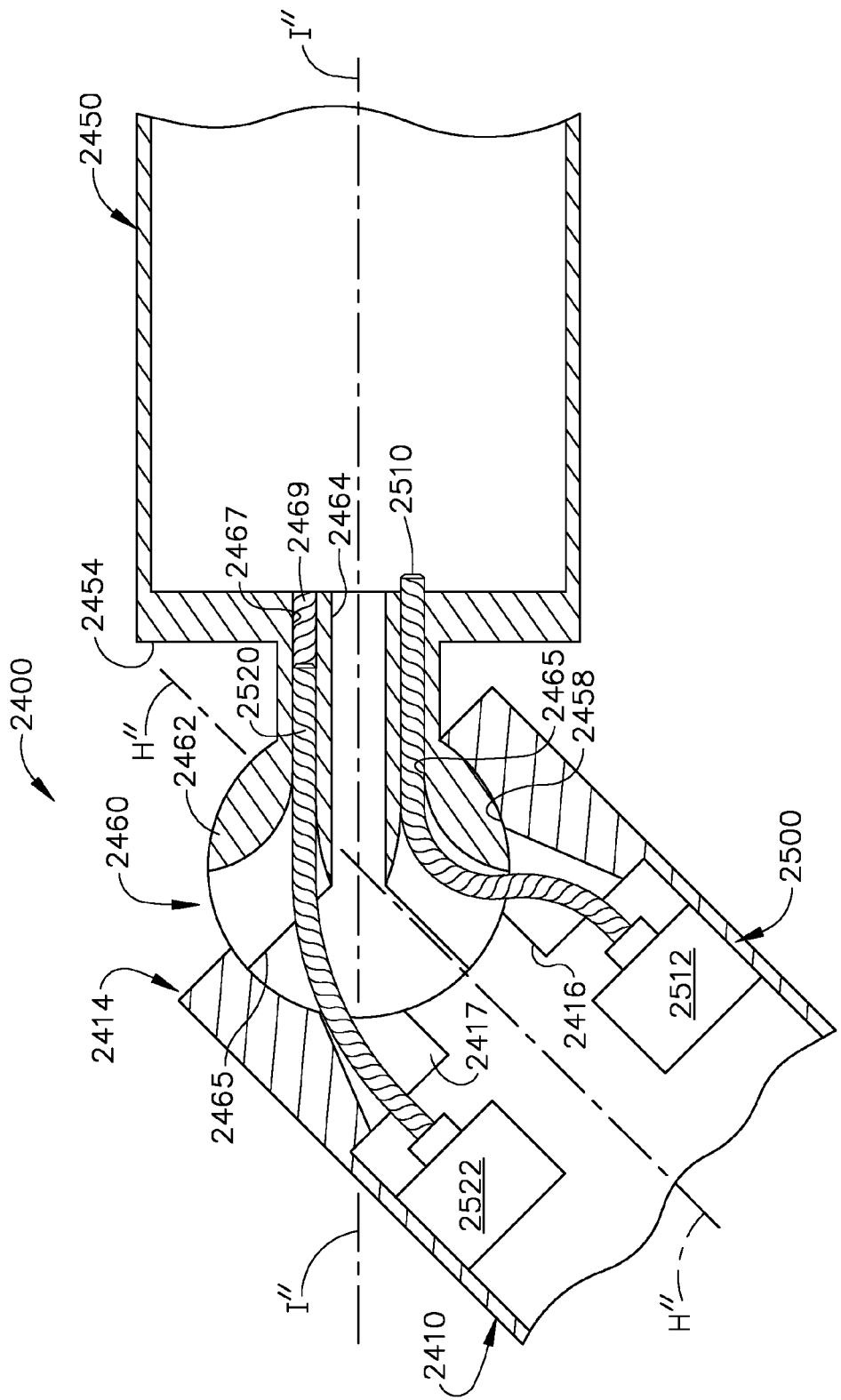
FIG. 17 is a partial cross-sectional view of another articulation joint embodiment of the present invention in an articulated position.

FIG. 17 illustrates yet another articulation joint assembly 2400 embodiment of the present invention. As can be seen in that Figure, distal tube segment 2410 has a proximal end 2414 and a distal axis H"-H". Although not shown in FIG. 17, the distal tube segment 2410 has a distal end that is mechanically coupled to the end effector body 24. Depending upon the anvil closure arrangement employed, the distal end may be non-movably attached to the end effector body or by a cable, flexible member or pivotable member. The distal tube 2410 segment may be partially hollow with the proximal end 2414 being solid with a hose/wire receiving passage 2416 therethrough. The passage 2416 may have a conical shaped portion 2417.

The joint assembly 2400 further includes a proximal tube segment 2450, that has a distal end 2454, and a proximal axis I"-I". Although not shown in FIG. 18, the proximal tube segment 2450 has a proximal end 2454 that is attached to the handle assembly 200.

In one embodiment, the distal tube segment 2410 is pivotally coupled to the proximal tube segment 2450 by a ball joint assembly 2460. In one embodiment, the ball joint assembly 2460 comprises a ball member 2462 that is mounted to or is formed on the distal end 2454 of the proximal tube segment 2450. The ball member 2462 has a hollow passageway 2464 that has a flared or otherwise enlarged end portion 2465 to enable it to communicate with the passageway portions 2416, 2417 such that, regardless of the position of the ball member 2462, the hoses 480 and/or wires extending therethrough will not be pinched or otherwise damaged. The ball member 2462 is received in a socket 2458 provided in the proximal end 2414 of the distal tube segment 2410, such that the ball member 2462 is free to rotate therein.

In one embodiment, an actuation assembly, generally designated as 2500 is employed to articulate the distal tube segment 2410 relative to the proximal tube segment 2450. As can be seen in FIG. 17, in one non-limiting embodiment, two flexible worm gear cables 2510, 2520 are employed. The first flexible worm gear cable 2510 is adapted to drivingly engage worm gear teeth, threads, etc. (not shown) within a first gear passage 2465 formed in the ball member 2462. The first flexible worm gear cable 2510 is coupled to a first motor 2512 that is mounted within the distal tube segment 2410. Similarly, in this non-limiting embodiment, a second flexible worm gear cable 2520 is adapted to drivingly engage gear teeth, threads, etc. within a second gear passage 2467 formed in the ball member 2462 that has worm gear teeth, threads, etc. 2469 formed therein. The second flexible worm gear cable 2520 is coupled to a second motor 2522 mounted in the distal tube segment 2410. While described herein as "flexible worm gear cables", it will be understood that this term is meant to encompass all types of flexible driven cable or driver arrangements that do not necessarily employ worm gear-type teeth thereon.

The first and second motors 2512, 2522 may be electrically powered (by battery 234 or another battery) or be powered by alternating current or be powered by hydraulic fluid or air. In one embodiment, the motors 2512, 2522 are electric powered and are operated by one or more switches or buttons (not shown) on handle assembly 200. By controlling the amount of rotation and the direction of rotation of the first and second worm gear cables 2510, 2520, the ball member 2462 is cause to rotate within the socket 2458 and thereby articulate the distal tube segment 2410 (and the end effector 22 attached thereto) relative to the proximal tube segment 2450. The reader will appreciate that such arrangement facilitates left articulation as shown in FIG. 17 and right articulation (not shown). Again, however, the reader will appreciate that, while two flexible worm gear cable/motor arrangements have been described above, other embodiments of the present invention may employ only one flexible worm gear cable arrangement if only one degree articulation is needed or desired. Also, while the ball member 2462 has been described as being non-movably mounted to the proximal tube segment 2450 with the socket 2458 provided in the distal tube segment 2410, those of ordinary skill in the art will understand that the ball member 2462 may be non-movably attached to the distal tube segment 2410 and the socket 2458 provided in the proximal tube segment 2450 in other non-limiting embodiments without departing from the spirit and scope of the present invention.

Figure 17A:
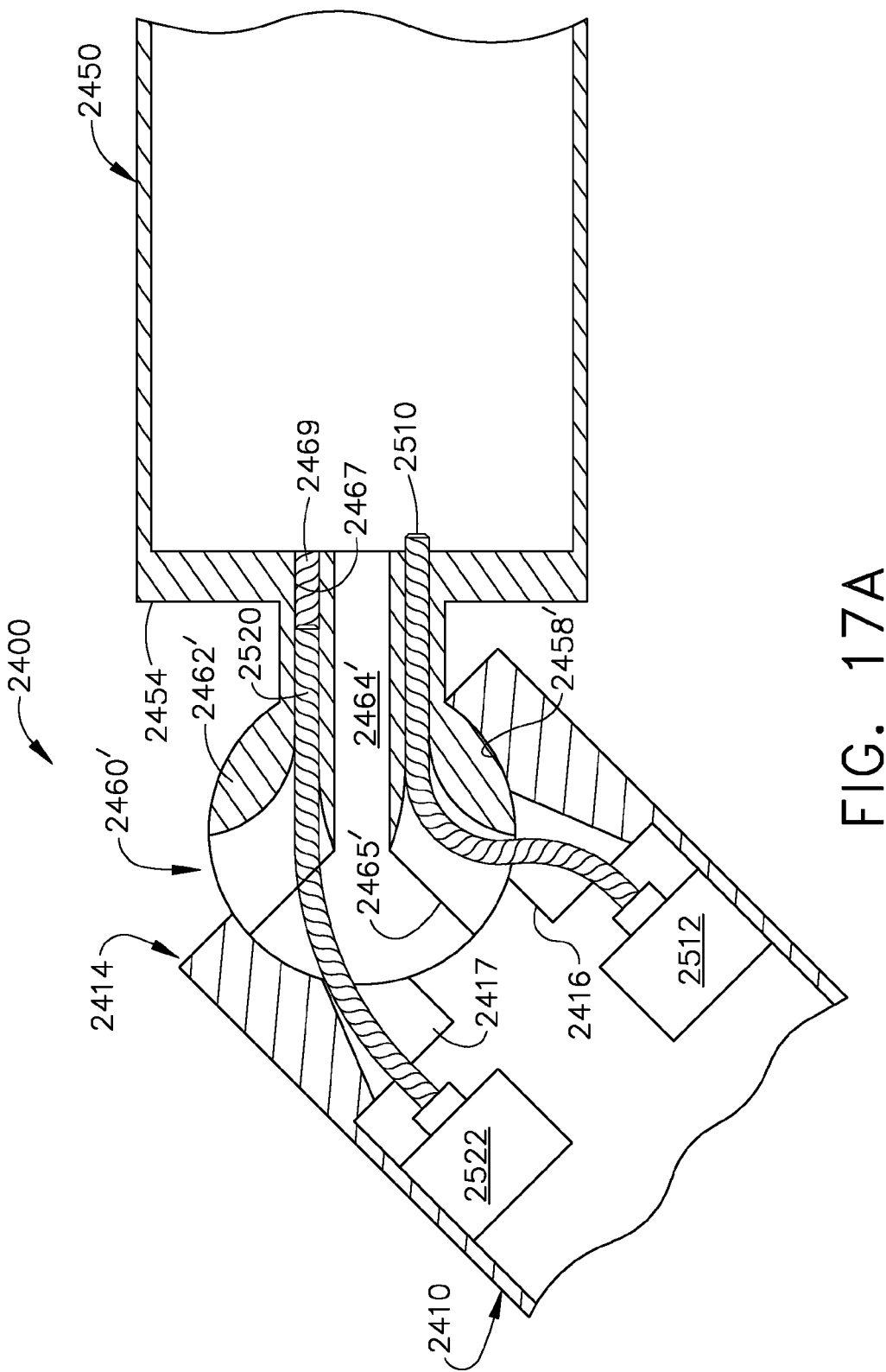
FIG. 17A is a partial cross-sectional view another articulation joint of the present invention in an articulated position.

In an alternative embodiment depicted in FIG. 17A, the joint assembly 2460' comprises a round disc-like member 2462' instead of a ball shaped member. The disc-like member 2462' has a hollow passageway 2464' that has a flared or otherwise enlarged end portion 2465' to enable it to communicate with the passageway 2416 such that, regardless of the position of the disc-like member 2462', the hoses 480 and/or wires extending therethrough will not be pinched or otherwise damaged. The disc-like member 2462' is received in a socket 2458' provided in the proximal end 2414 of the distal tube segment 2410, such that the disc-like member 2462' is free to rotate therein. If desired, the outer edge of the disc-like member 2462' could be provided with a tongue (not shown) that is received in a groove (not shown) in the socket wall to further stabilize the disc-like member 1462'. This embodiment otherwise employs the motor driven flexible worm gear cables 2510 and 2520 as described above. Again, however, the reader will appreciate that, while two flexible worm gear cable/motor arrangements have been described above, other embodiments of the present invention may employ only one flexible worm gear cable arrangement if only one degree articulation is needed or desired. Also, while the disc-like member 2462' has been described as being non-movably mounted to the proximal tube segment 2450 with the socket 2458' provided in the distal tube segment 2410, those of ordinary skill in the art will understand that the disc-like member 2462' may be non-movably attached to the distal tube segment 2410 and the socket 2458' provided in the proximal tube segment 2450 in other non-limiting embodiments without departing from the spirit and scope of the present invention.

The various non-limiting embodiments of the present invention provide a host of advantages over prior art articulated surgical instruments. In particular, the various embodiments of the subject invention enable the portions of the tube member that attach a surgical implement to a handle to be inserted through a trocar or similar device and then be selectively articulated within the patient. While the various embodiments have been described herein in connection with use with a hydraulically operated endocutter, those of ordinary skill in the art would appreciate that the various embodiments of the subject invention could be employed with electrically powered endocutters and with a host of other types of surgical implements, regardless of whether they are electrically or hydraulically powered.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. Accordingly, the present invention has been discussed in terms of endoscopic procedures and apparatus. However, use herein of terms such as "endoscopic" should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures. Moreover, the various embodiment of the present invention should not be limited solely to use in connection with surgical instruments that have hydraulically powered or air powered surgical implements. The various embodiments of the present invention may also be effectively used with surgical instruments and the like that employ electrically driven surgical implements.

What is claimed is:

1. A surgical instrument, comprising:
 a housing assembly;
 a proximal tube segment attached to said housing assembly and protruding distally out of said housing assembly;
 a distal tube segment;
 an articulating joint assembly pivotally coupling said distal tube segment to said proximal tube segment, said articulating joint assembly comprising:
  a first joint member non-movably coupled to one end of one of said proximal and distal tube segments and rotatably received in a corresponding socket in another end of the other of said proximal tube segment and distal tube segment; and
  at least one flexible cable attached to a motor, said flexible cable having a series of worm gear teeth thereon arranged to drivingly engage a corresponding passageway formed in the first joint member or socket for retaining a portion of said first joint member in said socket and, upon selective rotation, articulate said distal tube segment relative to said proximal tube segment; and
 a surgical implement attached to said distal tube segment.

2. The surgical instrument of claim 1 wherein said surgical implement comprises an endocutter end effector.

3. The surgical instrument of claim 1 wherein said first joint member has at least one hollow passage therethrough adapted to communicate with openings in said distal and proximal tube segments.

4. The surgical instrument of claim 1 wherein said motor is electrically powered.

5. The surgical instrument of claim 1 wherein said motor is powered by hydraulic fluid.

6. The surgical instrument of claim 1 wherein said motor is powered by air.

7. The surgical instrument of claim 1 wherein the first joint member comprises a ball member.

8. The surgical instrument of claim 1 wherein the first joint member comprises a disc-like member.

* * * * *